US007867734B2

(12) United States Patent
Nakano et al.

(10) Patent No.: US 7,867,734 B2
(45) Date of Patent: Jan. 11, 2011

(54) ANTI-GLYPICAN 3 ANTIBODY HAVING MODIFIED SUGAR CHAIN

(75) Inventors: Kiyotaka Nakano, Shizuoka (JP); Izumi Sugo, Shizuoka (JP); Masamichi Sugimoto, Kanagawa (JP); Takahiro Ishiguro, Kanagawa (JP); Megumi Tanaka, Shizuoka (JP); Shigeyuki Iijima, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 343 days.

(21) Appl. No.: 11/577,944

(22) PCT Filed: Oct. 26, 2005

(86) PCT No.: PCT/JP2005/020057

§ 371 (c)(1),
(2), (4) Date: Aug. 8, 2007

(87) PCT Pub. No.: WO2006/046751

PCT Pub. Date: May 4, 2006

(65) Prior Publication Data

US 2008/0124330 A1 May 29, 2008

(30) Foreign Application Priority Data

Oct. 26, 2004 (JP) ............................ 2004-311356

(51) Int. Cl.
*C12P 21/04* (2006.01)
*C07K 16/00* (2006.01)

(52) U.S. Cl. .................................. 435/69.6; 530/387.1

(58) Field of Classification Search ....................... None
See application file for complete search history.

(56) References Cited

U.S. PATENT DOCUMENTS

| | | | |
|---|---|---|---|
| 5,530,101 A | 6/1996 | Queen et al. | |
| 6,165,745 A | 12/2000 | Ward et al. | |
| 6,210,670 B1 | 4/2001 | Berg | |
| 6,737,056 B1 | 5/2004 | Presta | |
| 7,297,775 B2 | 11/2007 | Idusogie et al. | |
| 7,361,336 B1 | 4/2008 | Bergstein | |
| 7,427,400 B2 | 9/2008 | Bergstein | |
| 2004/0024320 A1 | 2/2004 | Karasawa et al. | |
| 2004/0236080 A1* | 11/2004 | Aburatani et al. | 530/388.26 |
| 2005/0171339 A1 | 8/2005 | Sugo et al. | |
| 2005/0233392 A1 | 10/2005 | Filmus et al. | |
| 2006/0024298 A1 | 2/2006 | Lazar et al. | |
| 2006/0040325 A1 | 2/2006 | Wu et al. | |
| 2006/0167232 A1 | 7/2006 | Aburatani et al. | |
| 2006/0188510 A1 | 8/2006 | Aburatani et al. | |
| 2006/0287508 A1 | 12/2006 | Sugo et al. | |
| 2007/0087005 A1 | 4/2007 | Lazar et al. | |
| 2007/0172488 A1 | 7/2007 | Aburatani et al. | |
| 2007/0190599 A1 | 8/2007 | Nakano et al. | |
| 2007/0269444 A1 | 11/2007 | Kinoshita et al. | |
| 2008/0008710 A1 | 1/2008 | Aburatani et al. | |
| 2008/0051563 A1 | 2/2008 | Lazar et al. | |
| 2008/0154025 A1 | 6/2008 | Lazar et al. | |
| 2008/0161541 A1 | 7/2008 | Lazar et al. | |
| 2008/0181890 A1 | 7/2008 | Lazar et al. | |
| 2008/0267979 A1 | 10/2008 | Lazar et al. | |

FOREIGN PATENT DOCUMENTS

| | | |
|---|---|---|
| AU | 2003261941 | 3/2004 |
| EP | 1176195 | 1/2002 |
| EP | 1411118 | 6/2002 |
| EP | 1331266 | 7/2003 |
| EP | 1462799 A1 | 9/2004 |
| EP | 1 464 702 | 10/2004 |
| EP | 1 498 491 | 1/2005 |
| EP | 1 541 680 | 6/2005 |
| EP | 1548442 A1 | 6/2005 |
| EP | 1561686 A1 | 8/2005 |
| EP | 1 671 645 | 6/2006 |
| EP | 1 674 111 | 6/2006 |
| EP | 1 800 693 | 6/2007 |
| EP | 1 816 140 | 8/2007 |

(Continued)

OTHER PUBLICATIONS

Yamane-Ohnuki, Kinoshita, Inoue-Urakubo, Kusunoki, Iida, Nakano, Wakitani, Niwa, Sakurada, Uchida, Shitara, Satoh. Establishment of FUT8 knockout CHO cells: an ideal host cell line for producing completely defucosylated antibodies with enhanced antibody-dependent cellular cytotoxicity. Biotechnology and Bioengineering, 2004. vol. 87, pp. 614-622.*

(Continued)

*Primary Examiner*—Anne M. Gussow
(74) *Attorney, Agent, or Firm*—Fish & Richardson P.C.

(57) ABSTRACT

An anti-glypican 3 antibody with modified sugar chains, more specifically, an anti-glypican 3 antibody lacking fucose is provided. The anti-glypican 3 antibody with modified sugar chains of the present invention may be produced by a process comprising introducing a nucleic acid encoding an anti-glypican 3 antibody into host cells with reduced fucose addition capability, such as YB2/0 cells and cells lacking a fucose transporter. The anti-glypican 3 antibody with modified sugar chains of the present invention has a high level of cytotoxic activity and therefore is useful as a cell growth inhibitor such as an anticancer agent.

8 Claims, 7 Drawing Sheets

FOREIGN PATENT DOCUMENTS

| | | |
|---|---|---|
| JP | 2-42355 | 2/1990 |
| JP | 4-336051 | 11/1992 |
| JP | 11-118775 | 4/1999 |
| JP | 2001-108661 | 4/2001 |
| JP | 2002-48867 | 2/2002 |
| JP | 2003-149213 | 5/2003 |
| JP | 2004-053360 | 2/2004 |
| WO | 9322332 | 11/1993 |
| WO | 9823289 | 6/1998 |
| WO | WO 99/54342 | 10/1999 |
| WO | WO 00/61739 | 10/2000 |
| WO | WO 02/22739 | 3/2002 |
| WO | WO 02/31140 | 4/2002 |
| WO | WO 02/079255 | 10/2002 |
| WO | WO 03/000883 | 1/2003 |
| WO | WO 03/042686 | 5/2003 |
| WO | WO 03/057881 | 7/2003 |
| WO | WO 03/074679 | 9/2003 |
| WO | WO 03/085119 | 10/2003 |
| WO | WO 03/100429 | 12/2003 |
| WO | WO 2004/018667 | 3/2004 |
| WO | WO 2004/022597 | 3/2004 |
| WO | WO 2004/022739 | 3/2004 |
| WO | WO 2004/022754 | 3/2004 |
| WO | WO 2004/023145 | 3/2004 |
| WO | WO 2004/038420 | 5/2004 |
| WO | WO 2004/099249 | 11/2004 |
| WO | WO 2005/023301 | 3/2005 |
| WO | WO 2006/006693 | 1/2006 |
| WO | WO 2006/022407 | 3/2006 |
| WO | WO 2006/046751 | 5/2006 |
| WO | WO 2007/047291 | 4/2007 |

OTHER PUBLICATIONS

Rudikoff, Giusti, Cook and Scharff. Single amino acid substitution altering antigen-binding specificity. Proceedings of the National Academy of Sciences, 1982. vol. 79, pp. 1979-1983.*

Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*

Burgess, Shaheen, Ravera, Jaye, Donohue, and Winkles. Possible dissociation of the heparin binding and mitogenic activities of heparin binding (acidic fibroblast) growth factor 1 from its receptor binding activities by site directed mutagenesis of a single lysine residue. Journal of Cell Biology, 1990. vol. 111, pp. 2129-2138.*

Lazar, Watanabe, Dalton, and Sporn. Transforming growth factor alpha: mutation of aspartic acid 47 and leucine 48 results in different biological activities. Molecular and Cellular Biology, 1988. vol. 8, pp. 1247-1252.*

Abe et al., "Matrixeye™ Portable 3D Ultrasonic Inspection System," *Toshiba Review*, 60:48-51, English abstract (2005).

Bendayan, "Possibilities of False Immunocytochemical Results Generated by the Use of Monoclonal Antibodies: the Example of the Anti-Proinsulin Antibody," *J. Histochem. Cytochem.*, 43:881-886 (1995).

Bost et al., "Antibodies Against a Peptide Sequence within the HIV Envelope Protein Crossreacts with Human Interleukin-2," *Immunol. Invest.*, 17:577-586 (1988).

Brorson et al., "Mutational Analysis of Avidity and Fine Specificity of Anti-Levan Antibodies," *J. Immunol.*, 163:6694-6701 (1999).

Brummell et al., "Probing the combining site of an anti-carbohydrate antibody by saturation-mutagenesis: role of the heavy-chain CDR3 residues," *Biochemistry*, 32:1180-87 (1993).

Burks et al., "In vitro scanning saturation mutagenesis of an antibody binding pocket," *Proc. Natl. Acad. Sci. USA*, 94:412-417 (1997).

Capurro et al., "Glypican-3: a novel serum and histochemical marker for hepatocellular carcinoma," *Gastroenterology*, 125:89-97 (2003).

Capurro et al., "Overexpression of Glypican-3 in Human Hepatocellular Carcinomas Determined by Immunohistochemistry Using a Monocolonal Antibody," *Proceedings of the Annual Meeting of the American Association for Cancer Research*, 93$^{rd}$ Annual Meeting, Apr. 6-10, 2002, 43:219 Abstract #1097 (2002).

Carter, "Improving the efficacy of antibody-based cancer therapies," *Nat. Rev. Cancer*, 1:118-129 (2001).

Casset et al., "A peptide mimetic of an anti-CD4 monoclonal antibody by rational design," *Biochem. Biophys. Res. Commun.*, 307:198-205 (2003).

Chen et al., "Selection and Analysis of an Optimized Anti-VEGF Antibody: Crystal Structure of an Affinity-Matured Fab in Complex with Antigen," *J. Mol. Biol.*, 293:865-881 (1999).

Colman, "Effects of amino acid sequence changes on antibody-antigen interactions," *Res. Immunol.*, 145:33-36 (1994).

De Pascalis et al., "Grafting of "Abbreviated" Complementarity-Determining Regions Containing Specificity-Determining Residues Essential for Ligand Contact to Engineer a Less Immunogenic Humanized Monoclonal Antibody," *J. Immunol.*, 169:3076-84 (2002).

Dennis, "Cancer: Off by a whisker," *Nature*, 442:739-741 (2006).

Dufner et al., "Harnessing phage and ribosome display for antibody optimization," *Trends Biotechnol.*, 24:523-529 (2006).

Filmus, "Glypicans in Growth Control and Cancer," *Glycobiology*, 11:19R-23R (2001).

Gonzalez et al., "OCI-5/GPC3, a Glypican Encoded by a Gene That is Mutated in the Simpson-Golabi-Behmel Overgrowth Syndrome, Induces Apoptosis in a Cell Line-Specific Manner,"*J. Cell Biol.*, 141:1407-14 (1998).

Gura, "Systems for Identifying New Drugs Are Often Faulty," *Science*, 278:1041-42 (1997).

Hippo et al., "Identification of Soluble $NH_2$-Terminal Fragment of Glypican-3 as a Serological Marker for Early-Stage Hepatocellular Carcinoma," *Cancer Res.*, 64:2418-23 (2004).

Holm et al., "Functional mapping and single chain construction of the anti-cytokeratin 8 monoclonal antibody TS1," *Mol. Immunol.*, 44:1075-84 (2007).

Huber, "Structure and Function of the Human Glypican 3 Gene," Washington University, Division of Biology and Biomedical Sciences Program in Molecular Genetics, St. Louis, Missouri (1998).

Jang et al., "The structural basis for DNA binding by an anti-DNA autoantibody," *Mol. Immunol.*, 35:1207-17 (1998).

Jiang et al., "Recurrence or metastasis of HCC: predictors, early detection and experimental antiangiogenic therapy," *World Journal of Gastroenterology*, 6:61-65 (2000).

Kobayashi et al., "Tryptophan H33 plays an important role in pyrimidine (6-4) pyrimidone photoproduct binding by a high-affinity antibody," *Protein Eng.*, 12:879-884 (1999).

Kumar et al., "Molecular Cloning and Expression of the Fabs of Human Autoantibodies in Escherichia coli," *J. Biol. Chem.*, 275:35129-36 (2000).

Lage et al., "Cloning and Characterization of Human cDNAs Encoding a Protein with High Homology to Rat Intestinal Development Protein OCI-5," *Gene*, 188:151-156 (1997).

Lage et al., "Expression of a Glypican-Related 62-kDa Antigen is Decreased in Hepatocellular Carcinoma in Correspondence to the Grade of Tumor Differentiation," *Virchows Arch*, 438:567-573 (2001).

Lund et al., "Multiple interactions of IgG with its core oligosaccharide can modulate recognition by complement and human Fcγ receptor I and influence the synthesis of its oligosaccharide chains," *J. Immunol.*, 157:4963-69 (1996).

MacCallum et al., "Antibody-antigen Interactions: Contact Analysis and Binding Site Topography," *J. Mol. Biol.*, 262:732-745 (1996).

Man et al., "Upregulation of Glypican-3 Expression in Hepatocellular Carcinoma but Downregulation in Cholangiocarcinoma Indicates its Differential Diagnosis Value in Primary Liver Cancers," *Liver International*, 25:962-966 (2005).

Midorikawa et al., "Glypican-3, Overexpressed in Hepatocellular Carcinoma, Modulates FGF2 and BMP-7 Signaling," *Int. J. Cancer*, 103:445-465 (2003).

MSNBC News Service, "Mixed results on new cancer drug," 4 pages (2000).

Nakatsura et al., "Glypican-3, overexpressed specifically in human hepatocellular carcinoma, is a novel tumor marker," *Biochem. Biophys. Res. Commun*., 306:16-25 (2003).
Niwa et al., "Defucosylated Chimeric Anti-CC Chemokine Receptor 4 IgG1 with Enhanced Antibody-Dependent Cellular Cytotoxicity Shows Potent Therapeutic Activity to T-Cell Leukemia and Lymphoma," Cancer Res., 64:2127-2133 (2004).
Pilia et al., "Mutations in GPC3, a Glypican Gene, Cause the Simpson-Golabi-Behmel Overgrowth Syndrome," *Nature Genetics*, 12:241-247 (1996).
Presta, "Engineering Antibodies for Therapy," *Curr. Pharm. Biotechnol*., 3:237-356 (2002).
Roskams et al., "Heparan sulphate proteoglycan expression in human primary liver tumours," *J. Pathol*., 185:290-297 (1998).
Sabit et al., "Enhanced expression of basement-membrane-type heparan sulfate proteoglycan in tumor fibro-myxoid stroma of intrahepatic cholangiocarcinoma," *Pathol. Int*., 51:248-256 (2001).
Seaver, "Monoclonal Antibodies in Industry: More Difficult Than Originally Thought," *Genetic Engineering*, 14:10, 21 (1994).
Shields et al., "Lack of Fucose on Human IgG1 N-Linked Oligosaccharide Improves Binding to Human Fcgamma RIII and Antibody-dependent Cellular Toxicity," *J Biol. Chem*., 277:26733-40 (2002).
Shinkawa et al., "The absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," *J. Biol. Chem*., 278:3466-73 (2003).
Smith-Gill et al., "Contributions of immunoglobulin heavy and light chains to antibody specificity for lysozyme and two haptens," *J Immunol*., 139:4135-44 (1987).
Song et al., "Light Chain of Natural Antibody Plays a Dominant Role in Protein Antigen Binding," *Biochem. Biophys. Res. Commun*., 268:390-394 (2000).
Steplewski et al., Biological activity of human-mouse IgG1, IgG2, IgG3, and IgG4 chimeric monoclonal antibodies with antitumor specificity, *Proc. Natl. Acad. Sci. USA*, 85:4852-56 (1988).
Sung et al., "Glypican-3 is overexpressed in human hepatocellular carcinoma," *Cancer Science*, 94:259-262 (2003).
Vajdos et al., "Comprehensive Functional Maps of the Antigen-binding Site of an Anti-ErbB2 Antibody Obtained with Shotgun Scanning Mutagenesis," *J. Mol. Biol*., 320:415-428 (2002).
Voskoglou-Nomikos et al., "Clinical Predictive Value of the in Vitro Cell Line, Human Xenograft, and Mouse Allograft Preclinical Cancer Models," *Clin. Cancer Res*., 9:4227-39 (2003).
Yamaguchi et al., "Current Status and Future Perspective of Biotherapy for Cancer," *Biotherapy*, 13:747-753 (1999) (English summary included).
Wichert et al., "Glypican-3 is involved in cellular protection against mitoxantrone in gastric carcinoma cells," *Oncogene*, 23:945-955 (2004).
Wu et al., "Humanization of a Murine Monoclonal Antibody by Simultaneous Optimization of Framework and CDR Residues," *J. Mol. Biol*., 294:151-162 (1999).
USPTO Restriction Requirement in U.S. Appl. No. 11/251,561, dated Dec. 13, 2007, 9 pages.
Fish & Richardson P.C., Response to Restriction Requirement dated Dec. 13, 2007 in U.S. Appl. No. 11/251,561, filed Feb. 12, 2008, 1 page.
USPTO Office Action in U.S. Appl. No. 11/251,561, dated May 14, 2008, 12 pages.
Fish & Richardson P.C., Amendment in Reply to Action dated May 14, 2008 in U.S. Appl. No. 11/251,561, filed Nov. 13, 2008, 8 pages.
USPTO Final Office Action in U.S. Appl. No. 11/251,561, dated Feb. 25, 2009, 13 pages.
International Search Report and Written Opinion for App. Ser. No. PCT/US2006/039682 dated Apr. 13, 2007, 13 pages.
USPTO Restriction Requirement in U.S. Appl. No. 10/583,795, dated Dec. 18, 2007, 5 pages.
Fish & Richardson P.C., Response to Restriction Requirement dated Dec. 18, 2007 in U.S. Appl. No. 10/583,795, filed Jan. 18, 2008, 19 pages.
USPTO Office Action in U.S. Appl. No. 10/583,795, dated Mar. 27, 2008, 42 pages.
Fish & Richardson P.C., Amendment in Reply to Action dated Mar. 27, 2008 in U.S. Appl. No. 10/583,795, filed Sep. 29, 2008, 46 pages.
USPTO Office Action in U.S. Appl. No. 10/583,795, dated Jan. 7, 2009, 25 pages.
Interview Summary in U.S. Appl. No. 10/583,795, dated Apr. 8, 2009, 2 pages.
Fish & Richardson P.C., Amendment in Reply to Action dated Jan. 7, 2009 in U.S. Appl. No. 10/583,795, filed Apr. 7, 2009, 13 pages.
Interview Summary in U.S. Appl. No. 10/583,795, dated Apr. 20, 2009, 2 pages.
USPTO Office Action in U.S. Appl. No. 10/583,795, dated Jun. 26, 2009, 19 pages.
Japanese Patent Office, International Search Report for App. Ser. No. PCT/JP2005/013103, mailed Oct. 25, 2005, 1 page.
International Preliminary Report on Patentability for App. Ser. No. PCT/JP2005/013103, dated Jan. 7, 2009, 4 pages.
European Search Report for App. Ser. No. EP 05 76 0156, dated Oct. 1, 2007, 15 pages.
USPTO Restriction Requirement in U.S. Appl. No. 10/570,647, dated Apr. 4, 2008, 6 pages.
Japanese Patent Office, International Search Report for App. Ser. No. PCT/JP2004/013183, mailed Nov. 30, 2004, 4 pages.
Japanese Patent Office, International Preliminary Report on Patentability for App. Ser. No. PCT/JP2004/013183, dated Sep. 1, 2005, 17 pages.
European Search Report for App. Ser. No. EP 04 77 2 922, dated Jun. 14, 2007, 2 pages.
USPTO Restriction Requirement in U.S. Appl. No. 11/574,091, dated Dec. 17, 2008, 8 pages.
Fish & Richardson P.C., Response to Restriction Requirement dated Dec. 17, 2008 in U.S. Appl. No. 11/574,091, filed Jun. 16, 2009, 1 page.
Japanese Patent Office, International Search Report for App. Ser. No. PCT/JP2005/015607, mailed Oct. 24, 2005, 3 pages.
European Search Report for App. Ser. No. EP 05 78 0979, dated Nov. 10, 2008, 5 pages.
Japanese Patent Office, International Search Report for App. Ser. No. PCT/JP2005/020057, mailed Jan. 24, 2006, 2 pages.
European Search Report for App. Ser. No. EP 05 80 0031, dated Jul. 31, 2009, 9 pages.
Search Report and Written Opinion for App. Ser. No. SG 200703074-5, mailed Jul. 21, 2008, 9 pages.
USPTO Office Action in U.S. Appl. No. 11/574,091, dated Sep. 2, 2009, 18 pages.
USPTO Notive of Allowance in U.S. Appl. No. 10/583,795, dated Mar. 10, 2010, 16 pages.
Fish & Richardson P.C., Amendement in Reply to Action dated Sep. 2, 2009 in U.S. Appl. No. 11/574,091, Mar. 2, 2010, 7 pages.
Fish & Richardson P.C., Replay to Action dated Feb. 25, 2009 in U.S. Appl. No. 11/251,561, filed Mar. 24, 2010, 4 pages.
Fish & Richardson P.C., Supplemental Amendement to Reply to Action dated Feb. 25, 2009 in U.S. Appl. No. 11/251,561, filed Mar. 26, 2010, 16 pages.
Davidson, Davidson & Kappel, LLC, Amendment in Reply to Office Action dated Sep. 1, 2009 in U.S. Appl. No. 10/526,741, filed Feb. 24, 2010, 10 pages.
Arii et al., "Characteristics of recurrent hepatocellular carcinoma in Japan and our surgical experience," J. Hepatobiliary Pancrea. Surg., 8:397-403 (2001).
Budhu et al., "The Molecular Signature of Metastases of Human Hepatocellular Carcinoma," Oncology, 69 (suppl 1):23-27 (2005).
Ghetie et al., "Multiple Roles for the Major Histocompatibility Complex Class I-Related Receptor FcRn," Annu. Rev. Immunol., 18:739-766 (2000).
Hinton et al,. "Engineered Human IgG Antibodies with Longer Serum Half-lives in Primates," J. Biol. Chem., 279:6213-16 (2004).
Kim et al., "Mapping the site on human IgG for binding of the MHC class I-related receptor, FcRn," Eur. J. Immunol., 29:2819-25 (1999).
Martin et al., "Crystal Structure at 2.8 A of an FcRn/Heterodimeric Fc Complex: Mechanism of pH-Dependent Binding," Mol. Cell, 7:867-877 (2001).

Medesan et al., "Delineation of the Amino Acid Residues Involved in Transcytosis and Catabolism of Mouse IgG1," J. Immunol., 158:2211-17 (1997).
Raghavan et al., "Fc Receptors and their Interactions with Immunoglobulins," Annu. Rev. Cell Dev. Biol., 12:181-220 (1996).
Tang et al., "Metastatic human hepatocellular carcinoma models in nude mice and cell line with metastatic potential," World J. Gastroenterol., 7:597-601 (2001).
Fish & Richardson P.C., Amendment in Reply to Action dated Jun. 26, 2009 in U.S. Appl. No. 10/583,795, filed Dec. 24, 2009, 17 pages.
USPTO Restriction Requirement in U.S. Appl. No. 10/526,741, dated Mar. 27, 2006, 5 pages.
Davidson, Davidson & Kappel, LLC, Response to Restriction Requirement dated Mar. 27, 2006 in U.S. Appl. No. 10/526,741, filed Apr. 25, 2006, 6 pages.
USPTO Office Action in U.S. Appl. No. 10/526,741, dated Jun. 14, 2006, 40 pages.
Davidson, Davidson & Kappel, LLC, Amendment in Reply to Office Action dated Jun. 14, 2006 in U.S. Appl. No. 10/526,741, filed Dec. 12, 2006, 18 pages.
USPTO Final Office Action in U.S. Appl. No. 10/526,741, dated Mar. 9, 2007, 17 pages.
Davidson, Davidson & Kappel, LLC, Amendment in Reply to Office Action dated Mar. 9, 2007 in U.S. Appl. No. 10/526,741, filed July 9, 2007, 9 pages.
USPTO Advisory Action in U.S. Appl. No. 10/526,741, dated Aug. 14, 2007, 3 pages.
Davidson, Davidson & Kappel, LLC, Amendment in Reply to Action dated Aug. 14, 2007 in U.S. Appl. No. 10/526,741, filed Sep. 6, 2007, 9 pages.
USPTO Office Action in U.S. Appl. No. 10/526,741, dated Nov. 21, 2007, 17 pages.
Davidson, Davidson & Kappel, LLC, Amendment in Reply to Action dated Nov. 21, 2007 in U.S. Appl. No. 10/526,741, filed Mar. 20, 2008, 10 pages.
USPTO Final Office Action in U.S. Appl. No. 10/526,741, dated Jul. 9, 2008, 11 pages.
Davidson, Davidson & Kappel, LLC, Amendment in Reply to Office Action dated Jul. 9, 2008 in U.S. Appl. No. 10/526,741, filed Jan. 5, 2009, 113 pages.
USPTO Advisory Action in U.S. Appl. No. 10/526,741, dated Jan. 21, 2009, 4 pages.
USPTO Office Action in U.S. Appl. No. 10/526,741, dated Sep. 1, 2009, 15 pages.
USPTO Office Action in U.S. Appl. No. 10/481,524, dated Apr. 3, 2006, 23 pages.
Davidson, Davidson & Kappel, LLC, Amendment in Reply to Office Action dated Apr. 3, 2006 in U.S. Appl. No. 10/481,524, filed Aug. 31, 2006, 9 pages.
USPTO Interview Summary in U.S. Appl. No. 10/481,524, dated Sep. 6, 2006, 3 pages.
USPTO Restriction Requirement in U.S. Appl. No. 10/481,524, Jan. 5, 2007, 4 pages.
USPTO Office Communication in U.S. Appl. No. 10/481,524, dated Jan. 23, 2007, 2 pages.
USPTO Restriction Requirement in U.S. Appl. No. 11/702,780, dated Jul. 24, 2007, 5 pages.
Davidson, Davidson & Kappel, LLC, Response to Restriction Requirement dated Jul. 24, 2007 in U.S. Appl. No. 11/702,780, filed Aug. 22, 2007, 4 pages.
USPTO Office Action in U.S. Appl. No. 11/702,780, dated Nov. 16, 2007, 9 pages.
USPTO Interview Summary in U.S. Appl. No. 11/702,780, dated Dec. 14, 2007, 4 pages.
Davidson, Davidson & Kappel, LLC, Amendment in Reply to Office Action dated Nov. 16, 2007 in U.S. Appl. No. 11/702,780, filed May 16, 2008, 11 pages.
USPTO Office Action in U.S. Appl. No. 11/702,780, dated Sep. 3, 2008, 9 pages.
Davidson, Davidson & Kappel, LLC, Amendment in Reply to Office Action dated Sep. 3, 2008 in U.S. Appl. No. 11/702,780, filed Dec. 29, 2008, 6 pages.
USPTO Advisory Action in U.S. Appl. No. 11/702,780, dated Jan. 13, 2009, 4 pages.
USPTO Office Action in U.S. Appl. No. 11/702,780, dated Apr. 2, 2009, 7 pages.
Davidson, Davidson & Kappel, LLC, Amendment in Reply to Office Action dated Apr. 2, 2009 in U.S. Appl. No. 11/702,780, filed Sep. 30, 2009, 215 pages.
USPTO Notice of Allowance in U.S. Appl. No. 11/702,780, dated Jan. 26, 2010, 5 pages.
Ohno et al., "Antigen-binding specificities of antibodies are primarily determined by seven residues of VH,"Proc. Natl. Acad. Sci. U.S.A., 82:2945-2949 (1985).
Roitt et al., "Immunology,"Moscow, 102, 106-107 (2000) (with English translation).

* cited by examiner

ANTI-GLYPICAN 3 ANTIBODY HAVING MODIFIED SUGAR CHAIN

CROSS-REFERENCE TO RELATED APPLICATIONS

This application is the National Stage of International Application No. PCT/JP2005/020057, filed on Oct. 26, 2005, which claims the benefit of Japanese Patent Application Serial No. 2004-311356, filed on Oct. 26, 2004. The contents of both of the preceding applications are hereby incorporated by reference in their entireties.

TECHNICAL FIELD

The present invention relates to an antibody to glypican 3 antigen (i.e., an anti-glypican 3 antibody) in which cytotoxic activity, especially antibody-dependent cellular cytotoxicity (ADCC) is enhanced, as well as a process for producing the antibody.

BACKGROUND ART

Glypican 3 (GPC3) is a member of the family of heparan sulfate proteoglycans present on the surface of cells. It has been suggested that GPC3 may be involved in cell division upon development and in cancer cell growth, but its function is still not well understood.

It has been discovered that a type of antibody that binds to GPC3 inhibits cell growth due to ADCC (antibody-dependent cellular cytotoxicity) activity and CDC (complement-dependent cytotoxicity) activity (WO 2003/00883). Furthermore, because GPC3 is cleaved in the body and secreted into the blood as a soluble form of GPC3, it has been suggested that cancer can be diagnosed using an antibody that can detect the soluble form of GPC3 (WO 2004/022739, WO 2003/100429, WO 2004/018667).

When developing an anticancer agent that utilizes antibody cytotoxic activity, preferably the antibody used will have a high level of ADCC activity. Therefore, an anti-GPC3 antibody with a high level of cytotoxic activity has been demanded.

Modification of antibody sugar chains are known to enhance its ADCC activity. For example, WO 99/54342 discloses that ADCC activity is enhanced by modifying antibody glycosylation. In addition, WO 00/61739 discloses that ADCC activity is regulated by controlling the presence or absence of fucose in antibody sugar chains. WO 02/31140 discloses producing an antibody having sugar chains that do not contain a-1,6 core fucose by producing that antibody in YB2/0 cells. WO 02/79255 discloses an antibody with sugar chains having bisecting GlcNAc. However, an anti-GPC3 antibody with enhanced ADCC activity due to sugar chain modification has not been disclosed so far.

DISCLOSURE OF THE INVENTION

The present invention provides an anti-GPC3 antibody composition with enhanced ADCC activity caused by the alteration of the sugar chain component thereof, as well as a process for producing such an antibody.

After various investigations, the inventors have discovered that an antibody targeting GPC3 with sugar chains lacking α-1,6 core fucose have a high level of cytotoxic activity. Thus, the present invention provides an anti-GPC3 antibody composition wherein the sugar chain component of the antibody has been altered, and more specifically, an antibody composition with a greater fraction of fucose deficient anti-GPC3 antibodies. The sugar chain-modified anti-GPC3 antibody composition of the present invention has a high level of cytotoxic activity, and therefore is useful as a cell growth inhibitor such as an anticancer agent.

The present invention also provides a process for producing an anti-GPC3 antibody composition wherein the sugar chain of the antibody is modified, comprising the steps of: introducing a nucleic acid encoding the anti-GPC3 antibody into a host cell with reduced fucose addition capability such as YB2/0 cells, and culturing the host cell to obtain the antibody. Preferably, the cell with reduced capability of adding fucose to sugar chains is a cell lacking a fucose transporter.

DETAILED DESCRIPTION OF THE INVENTION

The present invention features an anti-GPC3 antibody composition wherein the sugar chain component of the antibody has been modified. It is known that the structure of the sugar chain linked to an antibody has a significant effect on the expression of antibody cytotoxic activity. Sugar chains that is linked to an antibody include N-glycoside-linked sugar chains, which are attached to a nitrogen atom on the side chain of an asparagine residue on the antibody molecule, and O-glycoside-linked sugar chains, which are attached to a hydroxyl group on the side chain of a serine or threonine residue on the antibody molecule. The present invention is focused on the presence or absence of fucose in an N-glycoside-linked sugar chain.

Figure 1:
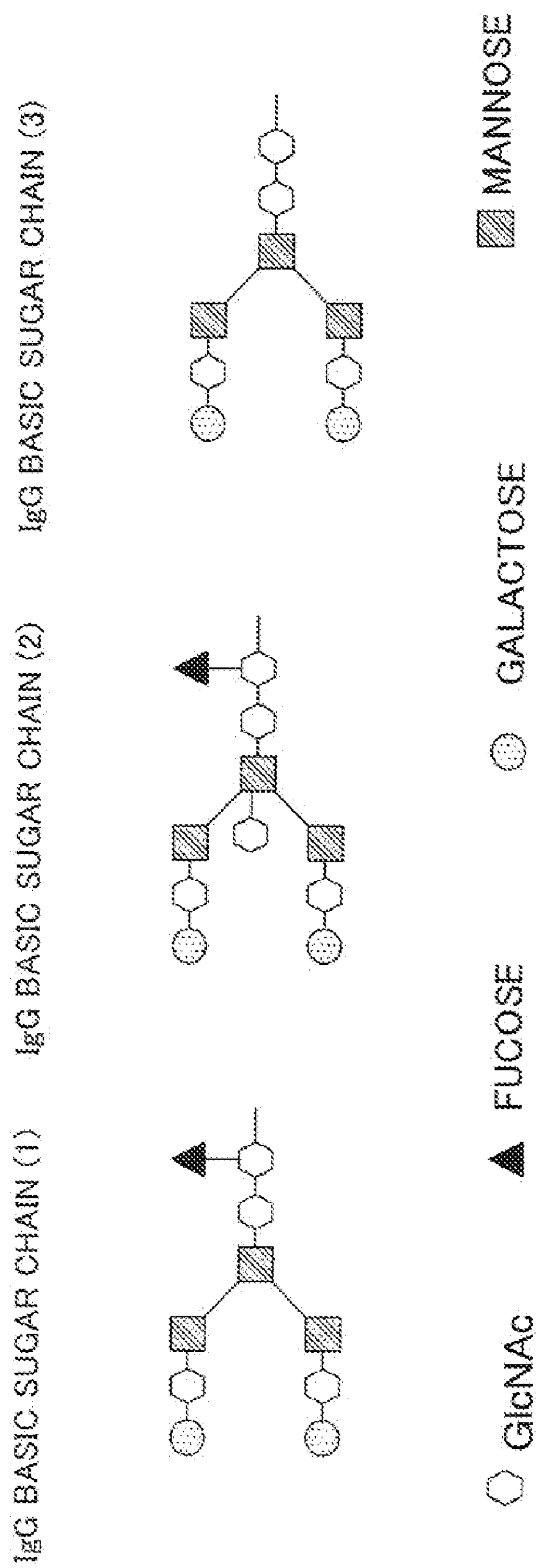
FIG. 1 shows the basic structure of N-glycoside linked sugar chains.

FIG. 1 shows the basic structure of N-glycoside-linked sugar chains attached to an antibody. As shown in the IgG basic sugar chains (1) and (3) of FIG. 1, the N-glycoside linked sugar chains have a basic structure (core) wherein one mannose (Man) and two N-acetylglucosamine (GlcNAc) moieties are linked by β-1,4 linkages [-Man β1-4GlcNAc β1-4GlcNAc-]. The "GlcNAc" on the right side of the structure is called the reducing end and the "Man" on the left side of the structure is called the non-reducing end. When a fucose is linked to the reducing end, it usually takes the form of an a-linkage between the 6-position of the N-acetylglucosamine at the reducing end and the 1-position of the fucose. On the other hand, in the sugar chain shown in IgG basic sugar chain (2) of FIG. 1, in addition to the aforementioned two sugar chains, one N-acetylglucosamine (GlcNAc) moiety is linked to the non-reducing end of the basic structure (core) via a β1,4-linkage. This type of N-acetylglucosamine (GlcNAc) is called a "bisecting N-acetylglucosamine." A sugar chain having a bisecting N-acetylglucosamine can be an O-glycoside-linked sugar chain or N-glycoside-linked sugar chains and it is formed by transfer of N-acetylglucosamine to the sugar chain by N-acetylglucosamine transferase III (GnTIII). The gene encoding this enzyme has already been cloned, and both the amino acid sequence and the nucleotide sequence of the DNA encoding the enzyme have already been reported (NCBI database (ACCESSION D13789)).

In the present invention, the antibody composition with a modified or altered sugar chain component (sugar chain-modified antibody composition) refers to an antibody composition having a sugar chain component that differs from the antibody composition produced by a host cell serving as a reference standard.

In the present invention, one may determine whether the sugar chain component has been modified or not by using as a reference standard the antibody composition produced by a host cell serving as a reference standard. If an antibody composition has a sugar chain component different from the antibody composition from the reference standard, that antibody composition is considered as an antibody composition with a modified sugar chain component.

The host cell serving as a reference standard in the present invention is CHO DG44 cell. CHO DG44 cell can be obtained, for example, from the Invitrogen Corporation.

Examples of an antibody composition with a modified sugar chain component include, for example, an antibody composition with an increased ratio of fucose (e.g., α-1,6 core fucose)-deficient antibodies in the antibody composition and an antibody composition with an increased ratio of antibodies having an attached bisecting N-acetylglucosamine (GlcNAc) in the antibody composition.

In a preferred embodiment of the present invention, the antibody composition has a higher ratio of fucose-deficient antibodies than the antibody composition used as a reference standard.

Because some antibodies have a plurality of N-glycoside sugar chains, the fucose-deficient antibody of the present invention encompasses not only antibodies wherein no fucose is attached, but also antibodies wherein the number of fucose moieties attached to the antibody is reduced (an antibody having at least one or more sugar chains wherein fucose is not present).

When manufacturing a sugar chain-modified antibody with host cells, it is often difficult to obtain a composition containing uniform antibodies wherein all antibodies have identical sugar chains. Therefore, if an antibody composition with a modified sugar chain component of the invention is an antibody composition with an increased ratio of fucose-deficient antibodies, for example, then the antibody composition with the modified sugar chain component of the present invention may contain both antibodies deficient in fucose and antibodies not deficient in fucose, but the overall ratio of antibodies deficient in fucose will be higher than in the antibody composition produced by the host cells serving as a reference standard. The present invention is not particularly limited to a specific ratio of fucose-deficient antibodies in the antibody composition with a high ratio of fucose-deficient antibodies of the present invention, but preferably the ratio is not less than 20%, more preferably not less than 50%, and most preferably not less than 90%.

The present invention is not particularly limited to a specific ratio of bisecting N-acetylglucosamine-added antibodies in the antibody composition having a high ratio of bisecting N-acetylglucosamine-added antibodies of the present invention, but preferably the ratio is not less than 20%, more preferably not less than 50%, and most preferably not less than 90%.

The anti-GPC3 antibody composition with a modified sugar chain component of the present invention can be obtained by methods known to those skilled in the art.

For example, a fucose-deficient antibody can be produced by expressing the anti-GPC3 antibody in host cells either lacking capability or having lower capability to add a-1,6 core fucose.

The present invention is not particularly limited to the host cells lacking capability or having lower capability to add fucose, but host cells with no or reduced fucose transferase activity, host cells with lower fucose concentration in Golgi bodies, and the like may be used in the present invention. More specifically, examples of host cells include rat myeloma YB2/3HL.P2.G11.16Ag.20 cells (abbreviated as YB2/0 cells) (preserved as ATCC CRL 1662), FTVIII knockout CHO cells (WO 02/31140), Lec13 cells (WO 03/035835) and fucose transporter deficient cells (WO 2005/017155).

As used herein, the term "fucose transporter deficient cell" refers to a cell in which the quantity of fucose transporter in the cell is less than in normal cells, or fucose transporter function is attenuated due to an abnormality in the fucose transporter structure. Examples of fucose transporter deficient cells may include, for example, those cells wherein the fucose transporter gene is knocked out (hereinafter called FT-KO cells), those wherein part of the fucose transporter gene is either lacking or mutated, those deficient in the fucose transporter gene expression system, and the like. The nucleotide sequence of the gene encoding the Chinese hamster fucose transporter and the amino acid sequence thereof are shown in SEQ ID NOS: 126 and 127, respectively.

Moreover, it is possible to obtain the fucose transporter deficient cell of the present invention using RNA interference (RNAi) by utilizing the nucleotide sequence represented by SEQ ID NO: 126. RNAi refers to the following phenomenon: when double stranded RNA (dsRNA) is introduced into a cell, intracellular mRNA matching that RNA sequence is specifically degraded and cannot be expressed as a protein. Normally dsRNA is used with RNAi, but the present invention is not limited thereto and, for example, double stranded RNA formed by self-complementary single stranded RNA molecules can also be used. With respect to the regions forming the double stranded molecule, the molecule may be double stranded in all regions, or may be single stranded in some regions (for example, one or both ends). The present invention is not limited to a specific length of the oligo-RNA used in RNAi. The length of the oligo-RNA in the present invention can be, for example, 5 to 1000 bases (or 5 to 1000 bp in a double stranded molecule), preferably 10 to 100 bases (or 10 to 100 bp in a double stranded molecule), and most preferably 15 to 25 bases (15 to 25 bp in a double stranded molecule); however, a length of 19 to 23 bases (19 to 23 bp in a double stranded molecule) is especially preferred.

The aforementioned RNAi process utilizes the phenomenon wherein dsRNA consisting of both sense RNA and antisense RNA homologous to a specific gene will destroy the homologous part of the transcript (mRNA) of that gene. dsRNA corresponding to the entire sequence of the fucose transporter gene may be used, or shorter dsRNA (for example, 21 to 23 bp) corresponding to part of the sequence (small interfering RNA; siRNA) may be used. The dsRNA can be directly transferred into the cell, or a vector producing dsRNA can be prepared and transferred into a host cell, and the dsRNA can then be produced within the cell. For example, all or part of the DNA encoding the fucose transporter gene can be inserted into a vector so that it forms an inverted repeat sequence, and that vector can then be transferred into a host cell. The RNAi procedure can be carried out in accordance with the descriptions in the following references: Fire A. et al., Nature (1998), 391, 806-811; Montgomery M. K. et al., Proc. Natl. Acad. Sci. USA (1998), 95, 15502-15507; Timmons L. et al., Nature (1998), 395, 854; Sanchez A. et al., Proc. Natl. Acad. Sci. USA (1999), 96, 5049-5054; Misquitta L. et al., Proc. Natl. Acad. Sci. USA (1999), 96, 1451-1456; Kennerdell J. R. et al., Cell (1998), 95, 1017-1026; Waterhouse P. M. et al., Proc. Natl. Acad. Sci. USA (1998), 95 13959-13964; and Wianny F. et al., Nature Cell Biol. (2000), 2, 70-75.

The fucose transporter deficient cells obtained by the RNAi procedure may be screened as indicated by the fucose transporter activity. Screening can also be carried out based on the transcription and expression of the fucose transporter gene indicated by Western blotting or Northern blotting.

An antibody with a bisecting N-acetylglucosamine (GlcNAc) added to the sugar chain can be produced by expressing the anti-GPC3 antibody in a host cell having the capability to form a bisecting N-acetylglucosamine (GlcNAc) structure on the sugar chain.

A method for producing an antibody with a bisecting N-acetylglucosamine-added sugar chain is already known (WO 02/79255). The host cell having the capability to form a bisecting N-acetylglucosamine (GlcNAc) structure on a sugar chain is not particularly limited in the present invention, but may include, for example, a host cell having an expression vector containing DNA encoding GnTIII. Therefore, an anti-GPC3 antibody having a bisecting N-acetylglucosamine-added sugar chain can be produced using a host cell containing both an expression vector with DNA encoding GnTIII and an expression vector encoding the anti-GPC3 antibody. The DNA encoding GnTIII and the gene encoding the anti-GPC3 antibody can both be present on the same vector or can be present on different vectors.

Another method for increasing the ratio of fucose-deficient antibodies or bisecting N-acetylglucosamine-added antibodies in the antibody composition is to increase the ratio of those antibodies in the composition by purifying the fucose-deficient antibodies or bisecting N-acetylglucosamine-added antibodies.

Sugar chain analysis can be carried out by any methods known to those skilled in the art. For example, a sugar chain can be released from an antibody by reacting the antibody with N-glycosidase F (Roche) and the like. Then the sugar chains can be desalted by solid phase extraction using a cellulose cartridge (Shimizu Y. et al., Carbohydrate Research 332 (2001), 381-388), concentrated and dried, and fluorescent labeled with 2-aminopyridine (Kondo A. et al., Agricultural and Biological Chemistry 54:8 (1990), 2169-2170). The reagent is removed from the pyridylamino-sugar chains (PA-sugar chains) by solid phase extraction with a cellulose cartridge, then the sugar chains are concentrated by centrifugation to obtain purified PA-sugar chains. The sugar chains may be assayed by reverse phase HPLC analysis using an octadecyl silane (ODS) column. The PA-sugar chains thus prepared may be analyzed by two dimensional mapping utilizing a combination of reverse phase HPLC analysis with an ODS column and normal phase HPLC analysis with an amine column.

The sugar chain-modified anti-GPC3 antibody of the present invention is not limited to any specific antibodies, provided it binds to GPC3. Preferably, a binding to GPC3 can be specific. Preferred anti-GPC3 antibodies of the present invention include those antibodies that have the complementarity determining region (CDR) sequence shown in Table 1 below.

TABLE 1

| Antibody | CDR | Amino acid sequence | SEQ ID NO: |
|---|---|---|---|
| M13B3 (H) | CDR1 | NYAMS | 5 |
| | CDR2 | AINNNGDDTYYLDTVKD | 6 |
| | CDR3 | QGGAY | 7 |
| M3BB (H) | CDR1 | TYGMGVG | 8 |
| | CDR2 | NIWWYDAKYYNSDLKS | 9 |
| | CDR3 | MGLAWFAY | 10 |
| M11F1 (H) | CDR1 | IYGMGVG | 11 |
| | CDR2 | NIWWNDDKYYNSALKS | 12 |
| | CDR3 | IGYFYPDY | 13 |
| M5B9 (H) | CDR1 | GYWMH | 14 |
| | CDR2 | AIYPGNSDTNYNQKFKG | 15 |
| | CDR3 | SGDLTGGLAY | 16 |
| M6B1 (H) | CDR1 | SYAMS | 17 |
| | CDR2 | AINSNGGTTYYPDTMKD | 18 |
| | CDR3 | HNGGYENYGWFAY | 19 |
| M10D2 (H) | CDR1 | SYWMH | 20 |
| | CDR2 | EIDPSDSYTYYNQKFRG | 21 |
| | CDR3 | SNLGDGHYRFPAFPY | 22 |
| L9G11 (H) | CDR1 | SYWMH | 20 |
| | CDR2 | TIDPSDSETHYNLQFKD | 23 |
| | CDR3 | GAFYSSYSYWAWFAY | 24 |
| GC33 (H) | CDR1 | DYEMH | 25 |
| | CDR2 | ALDPKTGDTAYSQKFKG | 26 |
| | CDR3 | FYSYTY | 27 |
| GC179 (H) | CDR1 | INAMN | 28 |
| | CDR2 | RIRSESNNYATYYGDSVKD | 29 |
| | CDR3 | EVTTSFAY | 30 |
| GC194 (H) | CDR1 | ASAMN | 31 |
| | CDR2 | RIRSKSNNYAIYYADSVKD | 32 |
| | CDR3 | DPGYYGNPWFAY | 33 |
| GC199 (H) | CDR1 | DYSMH | 34 |
| | CDR2 | WINTETGEPTYADDFKG | 35 |
| | CDR3 | LY | 36 |
| GC202 (H) | CDR1 | TYGMGVG | 8 |
| | CDR2 | NIWWHDDKYYNSALKS | 37 |
| | CDR3 | IAPRYNKYEGFFAF | 38 |
| M13B3 (L) | CDR1 | KSSQSLLDSDGKTYLN | 39 |
| | CDR2 | LVSKLDS | 40 |
| | CDR3 | WQGTHFPLT | 41 |
| M3B8 (L) | CDR1 | KASQDINNYLS | 42 |
| | CDR2 | RANRLVD | 43 |
| | CDR3 | LQCDEFPPWT | 44 |
| M11F1 (L) | CDR1 | RSSQSLVHSNGNTYLH | 45 |
| | CDR2 | KVSNRFS | 46 |
| | CDR3 | SQSTHVPWT | 47 |
| M5B9 (L) | CDR1 | RSSKSLLHSNGITYLY | 48 |
| | CDR2 | QMSNLAS | 49 |
| | CDR3 | AQNLELPYT | 50 |
| M6B1 (L) | CDR1 | KASQDINKNII | 51 |
| | CDR2 | YTSTLQP | 52 |
| | CDR3 | LQYDNLPRT | 53 |
| M10D2 (L) | CDR1 | RASHSISNFLH | 54 |
| | CDR2 | YASQSIS | 55 |
| | CDR3 | QQSNIWSLT | 56 |

TABLE 1-continued

| Antibody | CDR | Amino acid sequence | SEQ ID NO: |
|---|---|---|---|
| L9G11 (L) | CDR1 | RASESVEYYGTSLMQ | 57 |
| | CDR2 | GASNVES | 58 |
| | CDR3 | QQSRKVPYT | 59 |
| GC33 (L) | CDR1 | RSSQSLVHSNGNTYLH | 45 |
| | CDR2 | KVSNRFS | 46 |
| | CDR3 | SQNTHVPPT | 60 |
| GC179 (L) | CDR1 | KSSKSLLHSNGNTYLN | 61 |
| | CDR2 | WMSNLAS | 62 |
| | CDR3 | MQHIEYPFT | 63 |
| GC194 (L) 1 | CDR1 | RSSKSLLHSYDITYLY | 64 |
| | CDR2 | QMSNLAS | 49 |
| | CDR3 | AQNLELPPT | 65 |
| GC194 (L) 2 | CDR1 | SASSSVSYMY | 66 |
| | CDR2 | DTSNLAS | 67 |
| | CDR3 | QQWSSYPLT | 68 |
| GC199 (L) | CDR1 | KSSQSLLHSDGKTFLN | 69 |
| | CDR2 | LVSRLDS | 70 |
| | CDR3 | CQGTHFPRT | 71 |
| GC202 (L) | CDR1 | RSSQSIVHSNGNTYLE | 72 |
| | CDR2 | KVSNRFS | 46 |
| | CDR3 | FQGSHVPWT | 73 |

The antibodies with the CDR sequence listed in the above table have a high level of cytotoxic activity. The antibodies with the CDR sequence listed in the above table recognize epitopes of amino acids 524-563 on GPC3. Because antibodies that recognize epitopes of amino acids 524-563 have a high level of cytotoxic activity, they are preferred as the anti-GPC3 antibody of the present invention.

In one preferred embodiment of the present invention, the antibody composition having a modified sugar chain component of the present invention is characterized by exhibiting enhanced ADCC activity. In the present invention, whether the ADCC activity is enhanced or not may be determined by comparing the ADCC activity of the antibody composition of the present invention with that of the reference standard antibody composition. If the antibody composition of the present invention shows higher ADCC activity than the reference standard, the ADCC activity is said to be enhanced.

ADCC activity can be measured by a method known to those skilled in the art, for example, by mixing the anti-GPC3 antibody with effector cells and target cells, and then determining the level of ADCC. More specifically, mouse spleen cells, human monocytes isolated from peripheral blood (PBMC) and bone marrow and the like can be used as the effector cells and human cells expressing GPC3 such as human hepatocellular carcinoma cell-line HuH-7 can be used as the target cells. First the target cells are labeled with $^{51}$Cr, anti-GPC3 antibody is added, the cells are incubated, and then effector cells in a suitable ratio to the target cells are added, and they are incubated together. After incubation, the supernatant is collected, and the ADCC activity is measured by counting the radioactivity in the supernatant.

Anti-GPC3 Antibody

The anti-GPC3 antibody can be prepared by a method known to those skilled in the art. For example, the antibody can be prepared by using GPC3 as a sensitizing antigen for immunization in accordance with a conventional immunization method, fusing the immune cells with known parent cells by a conventional cell fusion procedure, and screening for monoclonal antibody producing cells by a conventional screening method. More specifically, monoclonal antibodies can be prepared in the following manner. First, the GPC3 to be used as a sensitizing antigen for antibody production is obtained by expressing GPC3 (MXR7) based on the gene/amino acid sequence disclosed in Lage, H. et al., Gene 188 (1997), 151-156. In other words, the gene sequence encoding GPC3 is inserted into a known expression vector. After suitable host cells are transformed with the vector, the target human glycipan 3 protein is purified from the host cells or culture medium supernatant by a known method. Next the purified GPC3 protein is used as a sensitizing antigen. Alternatively, a partial peptide of GPC3 can be used as the sensitizing antigen. In such a process the partial peptide can be obtained by chemical synthesis according to the amino acid sequence of human GPC3. The epitopes on the GPC3 molecule recognized by the anti-GPC3 antibody of the present invention are not limited, but the anti-GPC3 antibody of the present invention may recognize any epitope present on the GPC3 molecule. This is because the anti-GPC antibody exhibits the cell growth inhibitory activity through its ADCC activity, CDC activity, or inhibition of growth factor activity, and because cell growth can also be inhibited by the action of a cytotoxic substance such as a radioactive isotope, chemotherapy drug, bacterial toxin attached to the anti-GPC3 antibody. Therefore, the antigen for preparing the anti-GPC3 antibody of the present invention can be any fragment of GPC3 provided it contains an epitope present on the GPC3 molecule.

In an especially preferred embodiment, a peptide containing amino acids 524-563 can be used as the sensitizing antigen to generate an antibody that recognizes an epitope of amino acids 524-563 of GPC3.

The mammal used for immunization with the sensitizing antigen is not particularly limited in the present invention, but preferably it should be selected in consideration of the compatibility with the parent cells to be used in cell fusion, and may include a rodent, for example, a mouse, rat, or hamster, or a rabbit, monkey, and the like. The animal may be immunized with the sensitizing antigen using a known method. In general, for example, the mammal can be injected intraperitoneally or subcutaneously with sensitizing antigen. More specifically, the sensitizing antigen can be diluted and suspended in a suitable amount of phosphate buffered saline (PBS) or physiological saline, mixed with a suitable amount of conventional adjuvant such as Freund's complete adjuvant if desired, emulsified, and administered to the mammal multiple times every 4 to 21 days. In addition, a suitable vehicle can be used upon immunization with the sensitizing antigen.

After the mammal is immunized in the above manner, and the desired antibody level is detected in the serum, the immune cells are collected from the mammal and subjected to cell fusion. Spleen cells are especially preferred immune cells for cell fusion. Mammalian myeloma cells are used as the partner parent cells to be fused with the immune cells. Known cell lines suitable for use as the myeloma cells include, for example, P3 (P3x63Ag8.653) (J. Immunol. (1979) 123, 1548-1550), P3x63Ag8U.1 (Current Topics in Microbiology and Immunology (1978) 81, 1-7), NS-1 (Kohler. G. and Milstein, C. Eur. J. Immunol. (1976) 6, 511-519), MPC-11 (Margulies. D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), S194 (Trowbridge, I. S. J. Exp. Med. (1978) 148, 313-323), R210 (Galfre, G. et al., Nature (1979) 277, 131-133). The cell fusion of the immune cells and myeloma cells basically can be carried out in accordance with a known method, for example, the method described by Kohler and Milstein (Kohler. G. and Milstein, C., Methods Enzymol. (1981) 73, 3-46). More specifically, the cell fusion can be carried out, for example, in a conventional liquid culture medium containing a cell fusion promoter. Examples of the cell fusion promoting chemicals include Polyethylene glycol (PEG) and Sendai virus (HVJ) and the like. If desired, a supplemental agent such as dimethyl sulfoxide and the like may be added to increase fusion efficiency. The ratio of immune cells to myeloma cells may be established arbitrarily. For example, setting the ratio of immune cells with respect to myeloma cells at 1-fold to 10-fold is preferred. A conventional liquid culture medium used for culturing these types of cells, such as RPMI-1640 liquid medium, MEM liquid medium, or another liquid medium suitable for the growth of the myeloma cell line may be used as the liquid medium in the cell fusion procedure. A serum supplement such as fetal calf serum (FCS) can also be used together. In the cell fusion procedure, specified amounts of the immune cells and myeloma cells are thoroughly mixed in the liquid culture medium, and then PEG solution (for example, average molecular weight of about 1000 to 6000) that has been heated to 37° C. is normally added at a concentration of 30 to 60% (w/v) and mixed to allow for forming fused cells (hybridomas). Next, a suitable liquid culture medium is added and centrifuged to remove the supernatant. By repeating this procedure, any cell fusion chemicals unfavorable for the growth of hybridomas are removed. Hybridomas obtained in this manner are selected by culturing them in a conventional liquid selection medium such as HAT medium (a culture medium containing hypoxanthine, aminopterin, and thymidine). Culturing in the HAT medium is continued for a sufficient period of time (normally a few days to a few weeks) until cells other than the target hybridomas (non-fused cells) die off. Then, a conventional limiting dilution procedure is carried out, followed by screening and monocloning hybridomas that produce the target antibody. In addition to immunizing a non-human animal with the antigen to obtain the hybridomas as above, desired human antibodies having GPC3 binding activity can be obtained by sensitizing human lymphocytes with GPC3 in vitro, and then fusing the sensitized lymphocytes with immortalized human myeloma cells (see Japanese Patent Publication No. H1-59878). In addition, it is possible to administer GPC3 as an antigen to a transgenic animal having the complete repertoire of human antibody genes to generate cells producing anti-GPC3 antibodies, and collect human antibodies to GPC3 from immortalized cells (see International Patent Application No. WO 94/25585, WO 93/12227, NO 92/03918, and WO 94/02602). Hybridomas producing monoclonal antibodies prepared in the above manner can be subcultured in a conventional liquid culture medium, and may be preserved for a long period of time in liquid nitrogen.

Recombinant Antibodies

The monoclonal antibody used in the present invention is a recombinant monoclonal antibody, which can be produced by cloning the antibody gene from a hybridoma, inserting the gene into a suitable vector, and integrating the vector into a host cell (for example, see Vandamme, A. M. et al., Eur. J. Biochem. (1990) 192; 767-775, 1990). More specifically, the mRNA encoding the variable (V) region of the anti-GPC3 antibody is isolated from a hybridoma producing the anti-GPC3 antibody. mRNA can be isolated using a known method such as the guanidine ultracentrifugation method (Chirgwin, J. M. et al., Biochemistry (1979) 18, 5294-5299), and the AGPC method (Chomczynski, P., et al., Anal. Biochem. (1987) 162, 156-159) to prepare total RNA, and then preparing the target mRNA using an mRNA Purification Kit (Pharmacia) and the like. The mRNA can also be prepared directly by using a QuickPrep mRNA Purification Kit (Pharmacia). Then cDNA of the antibody V region is synthesized from the mRNA thus obtained using reverse transcriptase. cDNA can be synthesized using the AMV Reverse Transcriptase First-strand cDNA Synthesis Kit (Seikagaku Corporation), and the like. Also the 5'-RACE method using the 5'-AmpliFINDER RACE Kit (Clontech) and PCR can be used for cDNA synthesis and amplification (Frohman, M. A. et al., Proc. Natl. Acad. Sci. USA (1988) 85, 8998-9002, Belyavsky, A. et al., Nucleic Acids Res. (1989) 17, 2919-2932). The target DNA fragment is purified from the PCR product and ligated to the vector DNA. The desired recombinant vector is prepared by inserting those vectors. It is introduced into *E. coli* and the desired colony is selected to prepare a desired recombinant vector. The nucleotide sequence of the target DNA is confirmed by a known method such as the dideoxynucleotide chain termination method. After DNA encoding the V region of the target anti-GPC3 antibody is obtained, it is inserted into an expression vector containing DNA encoding the desired antibody constant region (C region). For the production of the anti-GPC3 antibody used in the present invention, the antibody gene is inserted into the expression vector so that it will be expressed under the control of an expression control region such as an enhancer, promoter, and the like. Next, the antibody is expressed by transforming a host cell with that expression vector. The antibody gene can be expressed in the host cells by inserting DNA encoding the antibody heavy chain (H chain) and light chain (L chain) into separate expression vectors and simultaneously transforming the host cells, or by inserting DNA encoding both the H chain and L chain into a single expression vector and transforming the host cells (see WO 94/11523). In addition, the recombinant antibody can be produced not only by using the aforementioned host cells, but also by using a transgenic animal. For example, the antibody gene can be inserted into the middle of a gene encoding a protein produced specifically in milk (such as goat β-casein) to prepare a fused gene. Then the DNA fragment containing the fused gene containing the antibody gene is injected into a goat embryo, and the embryo is implanted in a female goat. The desired antibody can be obtained from the milk produced by the transgenic goat born from the goat implanted with the embryo and the offspring thereof. Furthermore, suitable hormones can be used in the transgenic goat to increase the amount of milk containing the desired antibody that is produced by the transgenic goat (Ebert, K. M. et al., Bio/Technology (1994) 12, 699-702).

Altered Antibodies

In addition to the antibodies as described above, an artificially altered gene recombinant antibody such as a chimeric antibody, humanized antibody, and the like can be used in the present invention for the purpose of reducing the xenoantigenicity to humans. Such modified antibodies can be produced according to known methods. A chimeric antibody can be obtained by ligating DNA encoding the antibody V region obtained as described above with DNA encoding the human antibody C region, and then inserting the DNAs into an expression vector. The vector in which the DNAs are inserted is integrated into host cells to produce the antibody. A chimeric antibody useful in the present invention can be obtained using such a conventional method. A humanized antibody, also called a reshaped human antibody, comprises the CDR of an antibody from a non-human mammal such as a mouse grafted onto a human antibody CDR. The general genetic engineering methods for obtaining humanized antibodies are known in the art (see EP 125023 and WO 96/02576). More specifically, a DNA sequence designed to link the mouse antibody CDR and the human antibody framework region (FR) is synthesized by PCR using as primers a plurality of oligonucleotides prepared such that they have overlapped CDR and FR terminal regions (the method described in WO 98/13388). The framework region of the human antibody to be linked via the CDR is selected such that the CDR will form a suitable antibody binding site. If necessary, amino acids of the framework region in the variable region of the antibody may be substituted so that the reshaped human antibody CDR will form a suitable antibody binding site (Sato, K. et al., Cancer Res. (1993) 53, 851-856). A human antibody C region is used for the C region of the chimeric antibody and the humanized antibody. For example, Cγ1, Cγ2, Cγ3, and Cγ4 can be used in the H chain, and Cκ and Cλ can be used in the L chain. In addition, the human antibody C region can be modified to improve the stability or productivity of the antibody. The chimeric antibody comprises the variable region of an antibody from a non-human mammal and the constant region from a human antibody. On the other hand, the humanized antibody comprises the CDR of an antibody from a non-human mammal and the framework region and C region from a human antibody. Because the humanized antibody has lower antigenicity in the human body, it is more useful as the active ingredient in the therapeutic agent of the present invention.

Modified Antibodies

The antibody used in the present invention is not limited to a whole molecule of antibody, but it may be an antibody fragment or a modified form of an antibody, provided it binds to GPC3 and inhibits the activity of GPC3. The present invention also encompasses bivalent antibodies as well as monovalent antibodies. Examples of an antibody fragment include Fab, $F(ab')_2$, Fv, Fab/c having one Fab and a complete Fc, or a single chain Fv (scFv) wherein the Fv of an H chain or L chain is linked by a suitable ligand. More specifically, to produce an antibody fragment, the antibody can be treated with an enzyme such as papain or pepsin, or a gene encoding such an antibody fragment can be constructed, inserted into an expression vector, and expressed in a suitable host cell (see, for example, Co, M. S. et al., J. Immunol. (1994) 152, 2968-2976, Better, M. & Horwitz, A. H. Methods in Enzymology (1989) 178, 476-496, Academic Press, Inc., Plueckthun, A. & Skerra, A. Methods in Enzymology (1989) 178, 476-496, Academic Press, Inc., Lamoyi, E., Methods in Enzymology (1989) 121, 652-663, Rousseaux, J. et al., Methods in Enzymology (1989) 121, 663-669, Bird, R. E. et al., TIBTECH (1991) 9, 132-137). A scFv can be obtained by joining the H chain V region and L chain V region of an antibody. In a scFv, the H chain V region and L chain V region are joined by a linker, preferably a peptide linker (Huston, J. S. et al., Proc. Natl. Acad. Sci. U.S.A. (1988) 85, 5879-5883). The H chain V region and L chain V region in the scFv may be derived from any antibodies described herein. Any single chain peptide comprising 12 to 19 amino acid residues may be used as the peptide linker joining the V regions. DNA encoding scFv can be obtained by amplifying a fragment by PCR using as a template a DNA portion encoding all or a desired amino acid sequence of the sequences of DNA encoding the H chain or the H chain V region of the above-mentioned antibody and DNA encoding the L chain or the L chain V region of the above-mentioned antibody with a primer pair that defines the both ends thereof. Then the fragment is amplified with a combination of DNA encoding a peptide linker portion and a primer pair which defines both ends to be ligated to the H chain and the L chain. Once DNA encoding scFv is prepared, an expression vector containing the DNA and a host cell transformed with the expression vector can be obtained according to a standard method. The scFv can be obtained from such a host according to a standard method. These antibody fragments can be produced in a host by obtaining the gene thereof in the same manner as described above and by allowing it to be expressed. In the present invention, the term "antibody" also encompasses a fragment of the antibody. An anti-GPC3 antibody attached to various molecules such as PEG and the like can be used as a modified antibody. In the present invention, the term "antibody" also encompasses such a modified antibody. The modified antibody can be obtained by chemical modification of the antibody obtained as above. Methods for modifying antibodies have already been established in the art.

Furthermore, the antibody used in the present invention can be a bispecific antibody. A bispecific antibody may be an antibody having an antigen binding site that recognizes a different epitope on the GPC3 molecule, or it may be an antibody wherein one antigen binding site recognizes GPC3 and the other antigen binding site recognizes a cytotoxic substance such as a chemotherapy drug and cell-derived toxin. In such a case, the cytotoxic substance will act directly on cells expressing GPC3, and specifically lesion tumor cells, and suppress the growth of tumor cells. A bispecific antibody may be prepared by linking two types of antibody HL pairs. Also it may be obtained by preparing a bispecific antibody-producing fused cell through the fusion of hybridomas that produce different monoclonal antibodies. A bispecific antibody can also be prepared by genetic engineering methods.

Expression and Production of Recombinant Antibodies or Modified Antibodies

An antibody gene constructed as noted above can be expressed and obtained by known methods. In the case of mammalian cells, a common useful promoter, gene to be expressed, and a poly-A signal sequence downstream on the 3' end can be functionally linked together and expressed. For example, the human cytomegalovirus immediate early promoter/enhancer can be used as the promoter/enhancer. In addition, other promoters/enhancers that can be used to express the antibody of the present invention include viral promoters/enhancers of retrovirus, polyomavirus, adenovirus and simian virus 40 (SV40), or promoters/enhancers from mammalian cells such as human elongation factor 1a (HEF-1a). Antibodies can be readily expressed by the method of Mulligan et al. (Nature (1979) 277, 108) when SV40 promoter/enhancer is used, and by the method of Mizushima et al. (Nucleic Acids Res. (1990) 18, 5322) when HEF1α promoter/enhancer is used.

The antibody of the present invention may be produced using an eukaryotic expression system having the capability of adding a sugar chain to the expressed antibody. Eukaryotic cells include, for example, established mammalian cell lines and insect cell lines, animal cells, fungal cells, and yeast cells.

Preferably, the antibody of the present invention is expressed in mammalian cells, for example, CHO, COS, myeloma, BHK, Vero, or HeLa cells. The target antibody is produced by culturing the transformed host cells either in vitro or in vivo. The host cells may be cultured using known methods. For example, DMEM, MEM, RPMI-1640, or IMDM may be used as the culture medium, and a serum complement such as fetal calf serum (FCS) may be supplemented.

Isolation and Purification of Antibody

The antibody expressed and produced in the above manner can be separated from the host cells or host animals and purified to homogeniety. The antibody of the present invention can be separated and purified using an affinity column, for example, a protein A column such as Hyper D, POROS and Sepharose F. F. (Pharmacia). In addition, any conventional methods for protein separation and purification may be used in the invention. For example, the antibody can be isolated and purified by appropriately selecting and combining affinity columns such as Protein A column with chromatography columns, filtration, ultra filtration, salting-out and dialysis procedures (Antibodies A Laboratory Manual, Ed Harlow, David Lane, Cold Spring Harbor Laboratory, 1988). An antibody having a desired sugar chain can be separated with a lectin column by a method known in the art, and the method described in WO 02/30954.

Determination of Antibody Activity

The antigen binding activity (Antibodies: A Laboratory Manual. Ed Harlow, David Lane, Cold Spring Harbor Laboratory, 1988) and ligand receptor binding inhibition (Harada, A. et al., International Immunology (1993) 5, 681-690) of the antigen used in the present invention may be measured by known methods. ELISA (enzyme-linked immunosorbent assay), EIA (enzyme immunoassay), RIA (radioimmunoassay), or the fluorescent antibody technique can be used for measuring antigen binding activity of the anti-GPC3 antibody of the present invention. For example, EIA is carried out as follows. A sample containing the anti-GPC3 antibody, such as culture supernatant of anti-GPC3 antibody producing cells or purified antibody, is added to a plate coated with GPC3. A secondary antibody labeled with an enzyme such as alkaline phosphatase is added, the plate is incubated and washed, and then the enzyme substrate, such as p-nitrophenyl phosphate, is added and the optical absorption is measured to evaluate the antigen binding activity.

Pharmaceutical Composition

The present invention provides a pharmaceutical composition comprising the anti-GPC3 antibody with a modified sugar chain component of the present invention.

A pharmaceutical composition comprising the antibody composition of the present invention is useful for the prevention and/or treatment of diseases associated with cell growth such as cancer, and is particularly useful for the prevention and/or treatment of liver cancer. The pharmaceutical composition comprising the antibody of the present invention can be formulated by methods known to those skilled in the art. The pharmaceutical composition can be administered parenterally in the form of an injectable formulation comprising a sterile solution or suspension in water or another pharmaceutically acceptable liquid. For example, the pharmaceutical composition can be formulated by suitably combining the antibody with pharmaceutically acceptable vehicles or media, such as sterile water and physiological saline, vegetable oil, emulsifier, suspension agent, surfactant, stabilizer, flavoring excipient, diluent, vehicle, preservative, binder, followed by mixing in a unit dose form required for generally accepted pharmaceutical practices. The amount of active ingredient included in the pharmaceutical preparations is such that a suitable dose within the designated range is provided.

The sterile composition for injection can be formulated in accordance with conventional pharmaceutical practices using distilled water for injection as a vehicle.

For example, physiological saline or an isotonic solution containing glucose and other supplements such as D-sorbitol, D-mannose, D-mannitol, and sodium chloride may be used as an aqueous solution for injection, optionally in combination with a suitable solubilizing agent, for example, alcohol such as ethanol and polyalcohol such as propylene glycol or polyethylene glycol, and a nonionic surfactant such as polysorbate 80™, HCO-50 and the like.

Examples of oily liquid include sesame oil and soybean oil, and it may be combined with benzyl benzoate or benzyl alcohol as a solubilizing agent. Other items that may be included are a buffer such as a phosphate buffer, or sodium acetate buffer, a soothing agent such as procaine hydrochloride, a stabilizer such as benzyl alcohol or phenol, and an antioxidant. The formulated injection will normally be packaged in a suitable ampule.

Route of administration is preferably parenteral, for example, administration by injection, transnasal administration, transpulmonary administration, transcutaneous administration. Administration may be systemic or local by intravenous injection, intramuscular injection, intraperitoneal injection, subcutaneous injection.

A suitable means of administration can be selected based on the age and condition of the patient. A single dose of the pharmaceutical composition containing the antibody or a polynucleotide encoding the antibody can be selected from a range of 0.001 to 1000 mg/kg of body weight. On the other hand, it is also possible to select a dose in the range of 0.001 to 100000 mg/body, but the present invention is by no means limited to such numerical ranges. The dose and method of administration will vary depending on the weight, age, condition, and the like of the patient, and can be suitably selected as needed by those skilled in the art.

The content of all patents and reference documents expressly cited in the specification of this application are hereby incorporated by reference in its entirety. In addition, the content of the specification and drawings of Japanese Patent Application 2004-311356, which is the basis for the priority claim of this application, are hereby incorporated by reference in its entirety.

EXAMPLES

The present invention is explained in detail through the following examples, but is by no means limited to these examples.

Example 1

Preparation of Mouse Anti-GPC3 Antibody

A soluble GPC3 protein lacking the hydrophobic region of the C terminus (amino acids 564 to 580) was prepared as the immunizing protein for the preparation of the anti-GPC3 antibody for immunization. The MRL/MpJUmmCrj-lpr/lpr mouse (hereinafter referred to as MRL/lpr mouse, purchased from Charles River Japan), which is an autoimmune disease mouse, was used as the immunization animal. Immunization was started when the mice were 7 or 8 weeks old, and a preparation for initial immunization was adjusted to a dose of 100 μg/head soluble GPC3. An emulsion was prepared using Freund's complete adjuvant (FCA, Becton Dickinson), and injected subcutaneously. After a series of five immunizations, the final immunization dose was diluted in PBS to 50 μg/head, and injected intravenously via the caudal vein. On day 4 after the final immunization, the spleen cells were resected, mixed with mouse myeloma cells P3-X63Ag8U1 (hereinafter referred to as P3U1, purchased from ATCC) in a 2:1 ratio, and cell fusion was carried out by gradually adding PEG-1500

(Roche Diagnostics). Hybridomas were screened by ELISA using immunoplates with immobilized soluble GPC3 core protein. Positive clones were monocloned by the limiting dilution procedure. As a result, 11 clones of antibodies with strong GPC3 binding activity were obtained (M3C11, M13B3, M1E7, M3B8, M11F1, L9G11, M19B11, M6B1, M18D4, M5B9, and M10D2).

Among the anti-GPC3 antibodies obtained, M11F1 and M3B8 exhibited particularly strong CDC activity. Thus the GST fusion protein containing the M11F1 and M3B8 epitopes (GC-3), which is the fusion protein containing a peptide from 524 Ala to 563 Lys of GPC3 and GST was used as immunogens for immunization of 3 Balb/c (Charles River Japan) mice and 3 MRL/lpr mice. For the first immunization, a preparation of GC-3 at a concentration of 100 μg/head was emulsified with FCA and was injected subcutaneously. After two weeks, a preparation of 50 μg/head was emulsified with Freund's incomplete adjuvant (FIA) and was injected subcutaneously. After five immunizations, the final immunization (50 μg/head) was injected intravenously to all mice via the caudal vein, and subjected to the cell fusion. Hybridomas were screened by ELISA using immunoplates with immobilized soluble GPC3 core protein lacking the hydrophobic region of the C terminus (amino acids 564-580). Positive clones were monocloned by the limiting dilution procedure. As a result, 5 clones of antibodies with strong GPC3 binding activity (GC199, GC202, GC33, GC179, and GC194) were obtained.

The H chain and L chain variable regions were cloned and each sequence was determined by standard method. Furthermore, the CDR regions were determined by comparison with a known antibody amino acid sequence database and checking for homology. The sequences of the CDR regions are shown in Tables 1 and 2.

Example 2

Preparation of Anti-GPC3 Antibody Mouse-Human Chimeric Antibody

The variable region sequences of the H chain and L chain of anti-GPC3 antibody GC33 were ligated to the constant region sequences of human IgG1 and κ chain. PCR was carried out using a synthetic oligonucleotide complementary to the 5' terminal nucleotide sequence of the antibody H chain variable region having a Kozak sequence and a synthetic oligonucleotide complementary to the 3' terminal nucleotide sequence having an NheI site. The PCR product thus obtained was cloned into pB-CH vector wherein the human IgG1 constant region has been inserted into pBluescript KS+ vector (Toyobo Co., Ltd.). The mouse H chain variable region and the human H chain (γ1 chain) constant region were ligated via the NheI site. The H chain gene fragment thus prepared was cloned into the expression vector pCXND3. Furthermore, PCR was carried out using a synthetic oligonucleotide complementary to the 5' terminal nucleotide sequence of the L variable region of the antibody having a Kozak sequence and a synthetic oligonucleotide complementary to the 3' terminal nucleotide sequence having a BsiWI site. The PCR product thus obtained was cloned into pB-CL vector wherein the human κ chain constant region has been inserted into pBluescript KS+ vector (Toyobo Co., Ltd.). The human L chain variable region and the constant region were ligated via the BsiWI site. The L chain gene fragment thus prepared was cloned into the expression vector pUCAG. The pUCAG vector is a vector prepared by digesting pCXN (Niwa et al., Gene, 1991, 108, 193-200) with the restriction enzyme BamHI to prepare a 2.6 kbp fragment, which was ligated to the restriction enzyme BamHI site of pUC19 vector (Toyobo Co., Ltd.)

To prepare the anti-GPC3 mouse-human chimeric antibody expression vector, a gene fragment was obtained by digesting pUCAG vector, in which the L chain gene fragment was inserted, with the restriction enzyme HindIII (Takara Shuzo Co., Ltd). This gene fragment was ligated to the restriction enzyme HindIII cleavage site of pCXND3 containing the H chain gene, and then cloned. The plasmid thus obtained expressed the neomycin resistance gene, DHFR gene, and anti-GPC3 mouse-human chimeric antibody gene in animal cells. (The amino acid sequence of the H chain variable region is shown in SEQ ID NO: 3, and the amino acid sequence of the L chain variable region is shown in SEQ ID NO: 4.)

Example 3

Preparation of Low-Fucose Type Anti-GPC3 Chimeric Antibody

First YB2/0 (ATCC, CRL-1662) cells were cultured as the host cells in RPMI-1640 medium containing 10% FBS. Then 25 μg of the anti-GPC3 chimeric antibody expression vector prepared in Example 2 was introduced into the YB2/0 cells (ATCC CRT-1662) by electroporation at a concentration of $7.5\times10^6$ cells/0.75 mL PBS(−) at 1.4 kV and 25 μF. After a recovery period of 10 min at room temperature, the cells treated by electroporation were suspended in 40 mL of RPMI-1640 medium containing 10% FBS. A 10-fold dilution was prepared using the same medium, and the cells were aliquoted into a 96-well culture plate at 100 μL/well. After culturing for 24 h in a $CO_2$ incubator (5% $CO_2$), Geneticin (Invitrogen Corp.) was added at a concentration of 0.5 mg/mL, and the cells were cultured for 2 weeks. Cell lines with a high level of chimeric antibody expression were screened using sandwich ELISA with anti-human IgG antibody, and cell lines stably expressing the antibody were established. Each anti-GPC3 mouse-human chimeric antibody was purified using Hi Trap ProteinG HP (Amersham).

Example 4

Measurement of ADCC Activity Using PBMC from Human Peripheral Blood

Preparation of Human PBMC Solution

Heparin-added peripheral blood collected from a healthy adult was diluted 2-fold with PBS(−), and layered on Ficoll-Paque™ PLUS (Amersham). After centrifugation (500×g, 30 min, 20° C.), the intermediate layer, which is the mononuclear cell fraction, was isolated. After the layer was washed 3 times, the cells were suspended in 10% FBS/RPMI to prepare a human PBMC solution.

Preparation of Target Cells

HepG2 cells (ATCC) and HuH-7 cells (Health Science Research Resources Bank) cultured in 10% FBS/RPMI-1640 medium were detached from the dish using Cell Dissociation Buffer (Invitrogen), aliquoted into a 96-well U-bottomed plate (Falcon) at a concentration of $1\times10^4$ cells/well, and cultured for one day. After culturing, 5.55 MBq of $^{51}Cr$ was added, and the cells were cultured for 1 h at 37° C. in a 5% $CO_2$ gas incubator. The cells were washed once with culture medium, and 50 μL of 10% FBS/RPMI-1640 medium was added to prepare the target cells.

Chromium Release Assay (ADCC Activity)

A volume of 50 μL of antibody solution prepared at various concentrations was added to the target cells, and allowed for reacting on ice for 15 min. Then 100 μL of human PBMC solution ($5\times10^5$ cells/well) was added, and the cells were incubated for 4 h at 37° C. in a 5% $CO_2$ gas incubator. After culturing, the plate was centrifuged and the radioactivity in 100 μL of culture supernatant was measured with a gamma-counter. The specific chromium release rate was determined by the following formula. Specific chromium release rate (%)=(A−C)×100/(B−C) In this formula, A represents the mean value of radioactivity (cpm) in each well; B represents the mean value of radioactivity (cpm) in a well wherein 100 μL of 2% NP-40 aqueous solution (Nonidet P-40, Code No. 252-23, Nacalai Tesque) and 50 μL of 10% FBS/RPMI medium were added to the target cells; and C represents the mean value of radioactivity (cpm) in a well wherein 150 μL of 10% FBS/RPMI medium was added to the target cells. The assay was conducted in triplicate, and the means and standard deviations of ADCC activity (%) were calculated.

Figure 2:
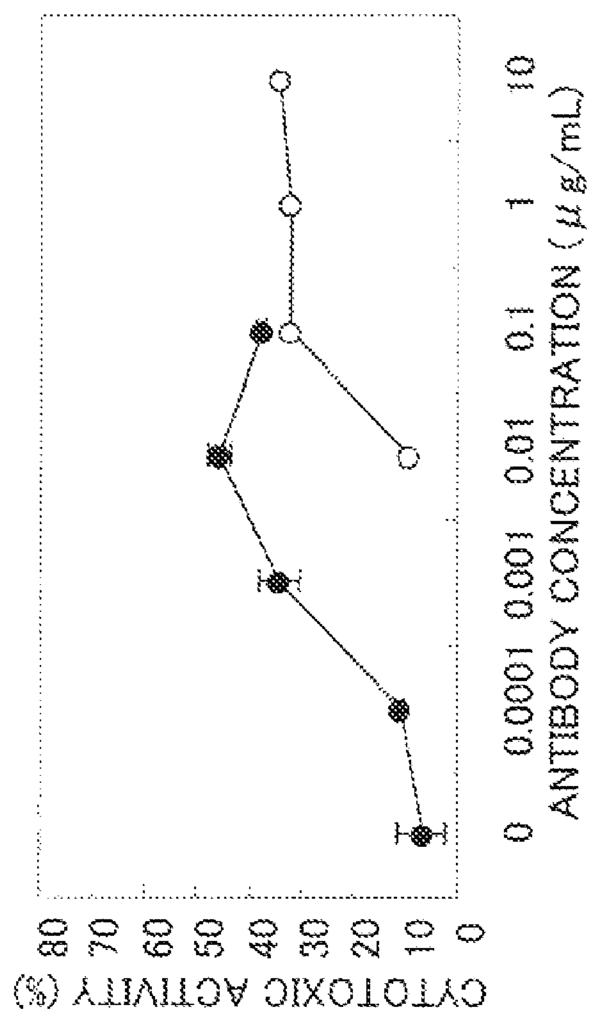
FIG. 2 shows ADCC activity of a chimeric antibody when HepG2 cells are targeted using human peripheral blood monocytes (PBMC)
Figure 3:
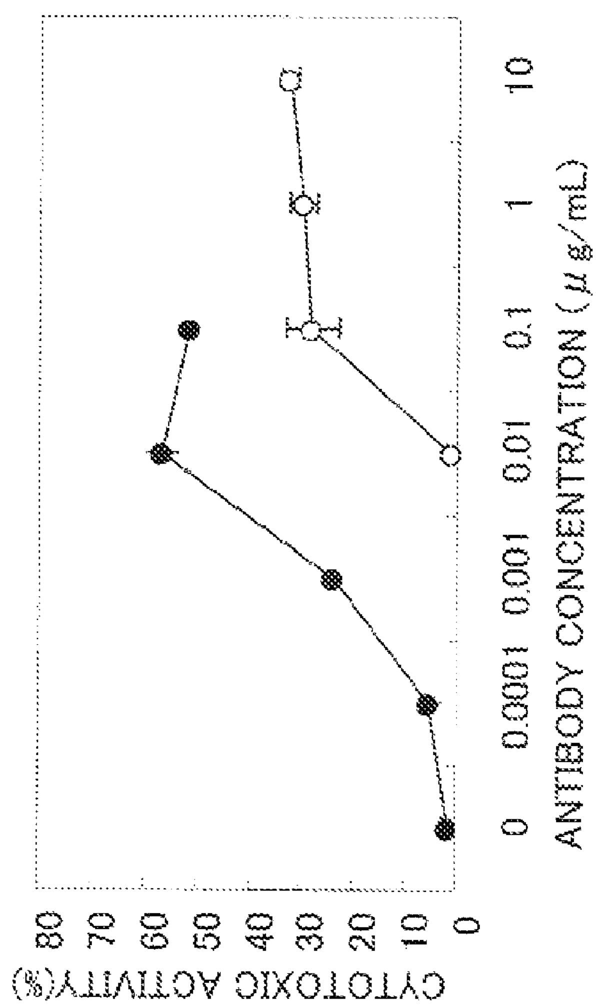
FIG. 3 shows ADCC activity of a chimeric antibody when HuH-7 cells are targeted using human PBMC.

FIGS. 2 and 3 show the ADCC activity of the anti-GPC3 chimeric antibody measured using PBMC. In the figures, the vertical axis represents cytotoxic activity (%) and the horizontal axis represents the concentration (μg/mL) of antibody added. FIG. 2 shows the results when HepG2 cells are used as the target cells and FIG. 3 shows the results for HuH-7 cells. The open circles show the activity of chimeric GC33 antibody produced by CHO cells, and the filled circles show the activity of chimeric GC33 antibody produced by YB2/0 cells. The low fucose type GC33 chimeric antibody produced by the YB2/0 cells shows stronger ADCC activity than the GC33 chimeric antibody produced by CHO cells, clearly indicating that ADCC activity of the anti-GPC3 antibody is enhanced by sugar chain modification.

Example 5

Establishment of Antibody Producing Cells

Hygromycin B was added to SFMII(+) medium at a final concentration of 1 mg/mL, and a fucose transporter deficient cell line (clone 3F2) was subcultured in the medium. A suspension of 3F2 cells in Dulbecco phosphate buffer ($8\times10^6$ cells/0.8 mL) was prepared. To the cell suspension, 25 μg of antibody expression vector was added (Reference Examples 1 and 2), and the cell suspension was transferred to a Gene Pulser Cuvette. After the cuvette was let stand on ice for 10 min, the vector was introduced into the cells by electroporation using a GENE-PULSER II at 1.5 kV and 25 μFD. The cells were suspended in 40 mL of SFMII(+) medium and transferred to a 96-well flat bottom plate (Iwaki) at 100 μL/well. After the plate was incubated in a $CO_2$ incubator for 24 h at 37° C., Geneticin (Invitrogen, Cat. No. 10131-027) was added at a final concentration of 0.5 mg/mL. The amount of antibody produced by the drug-resistant cells was measured to establish humanized anti-GPC3 antibody producing cell lines.

Example 6

Antibody Purification

The supernatant from the antibody expressing cell line was collected and loaded on Hitrap™ rProtein A column (Pharmacia Cat. No. 17-5080-01) using a P-1 pump (Pharmacia). After the column was washed with a binding buffer (20 mM sodium phosphate (pH 7.0)), and the protein was eluted with an elution buffer (0.1 M Glycin-HCl (pH 2.7)). The eluate was immediately neutralized with neutralizing buffer (1 M Tris-HCl (pH 9.0)). The antibody elution fractions were selected by DC protein assay (BIO-RAD Cat. No. 500-0111) and pooled, and were concentrated to about 2 mL with a Centriprep-YM10 (Millipore Cat. No. 4304). Next, the antibodies were separated by gel filtration using a Superdex 200 26/60 column (Pharmacia) equilibrated with 20 mM acetate buffer with 150 mM NaCl (pH 6.0). The monomer fraction peaks were collected, concentrated with Centriprep-YM10, and filtered through MILLEX-GW 0.22 μm Filter Unit (Millipore Cat. No. SLGV 013SL), and then preserved at 4° C. The absorption at 280 nm was measured and the concentration of purified antibody was calculated from the molar absorption coefficient.

Example 7

Figure 4:
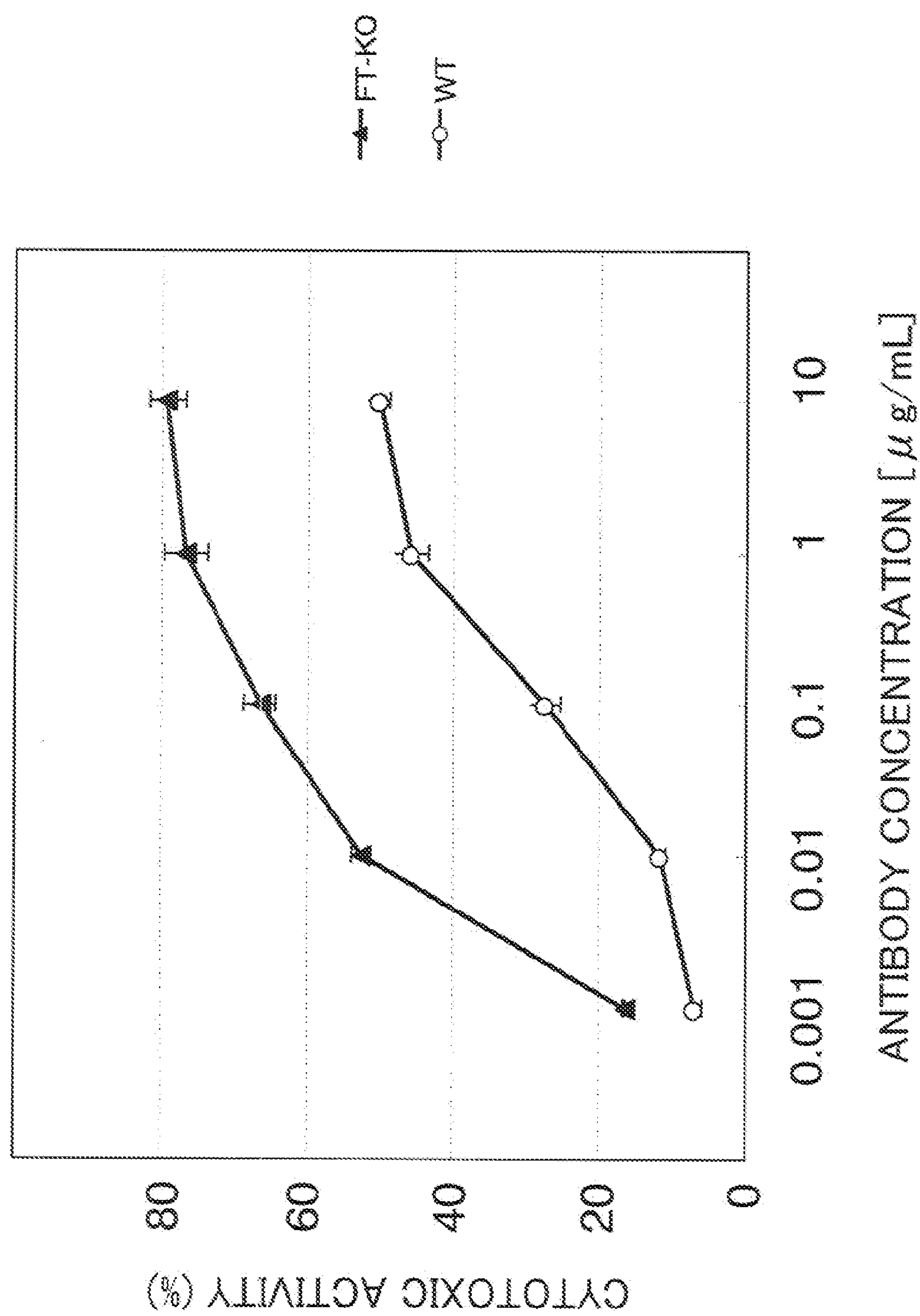
FIG. 4 shows ADCC activity of antibodies when HuH-7 cells are targeted using human PBMC.

In Vitro ADCC Activity of Humanized Anti-GPC3 Antibody Produced by FT-KO Cells FIG. 4 shows the in vitro ADCC activity of anti-GPC3 antibody produced by FT-KO cells when human PBMC is used. The method is as described in Example 4. In the figure, the vertical axis represents cytotoxic activity (%) and the horizontal axis represents the concentration (μg/mL) of antibody added. HuH-7 cells were used as the target cells. The open circles show the activity of anti-GPC3 antibody produced by wild type CHO cells, and the filled circles show the activity of anti-GPC3 antibody produced by FT-KO cells. The low fucose type anti-GPC3 antibody produced by the FT-KO cells shows stronger ADCC activity than the anti-GPC3 antibody produced by wild type CHO cells, clearly indicating that ADCC activity of the anti-GPC3 antibody produced by FT-KO cells is enhanced.

Example 8

Analysis of Sugar Chains of Humanized Anti-GPC3 Antibody Produced by FT-KO Cells 1. Preparation of 2-Aminobenzamide-Labeled Sugar Chains (2-AB Labeled Sugar Chains)

The antibodies produced by the FT-KO cells of the present invention and antibodies produced by CHO cells as a control sample were treated with N-Glycosidase F (Roche Diagnostics) to release the sugar chains from the protein (Weitzhandler M. et al., Journal of Pharmaceutical Sciences 83:12 (1994), 1670-1675). After removing the protein with ethanol (Schenk B. et al., The Journal of Clinical Investigation 108:11 (2001), 1687-1695), the sugar chains were concentrated and dried, and fluorescent labeled with 2-aminopyridine (Bigge J. C. et al., Analytical Biochemistry 230:2 (1995), 229-238). The reagent was removed from the 2-AB labeled sugar chains by solid phase extraction using a cellulose cartridge, and after concentration by centrifugation, purified 2-AB labeled sugar chains were obtained. Next, the purified 2-AB labeled sugar chains were treated with β-galactosidase (Seikagaku Corp.) to obtain agalactosyl 2-AB labeled sugar chains.

2. Analysis of Agalactosyl 2-AB Labeled Sugar Chains by Normal Phase HPLC

The antibodies produced by the FT-KO cells of the present invention and the antibodies produced by the CHO cells as a control sample were prepared as agalactosyl 2-AB labeled sugar chains according to the above method, and analyzed by normal phase HPLC using an amide column (Tosoh Corp.

Figure 5:
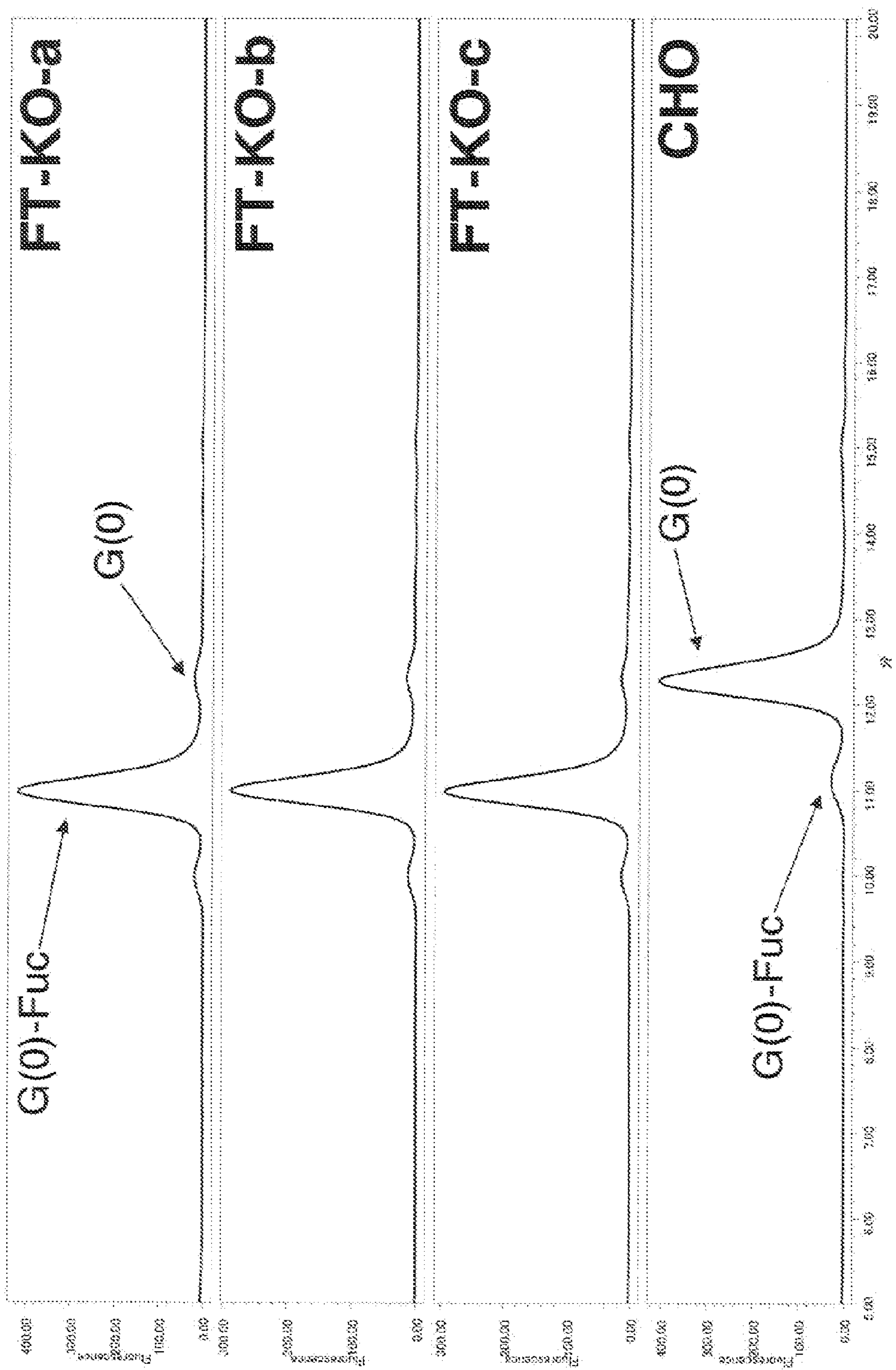
FIG. 5 shows normal phase HPLC chromatograms of sugar chains modified by agalactosyl 2-AB prepared from antibodies (a, b, c) produced by FT-KO cells and by CHO cells.
Figure 6:
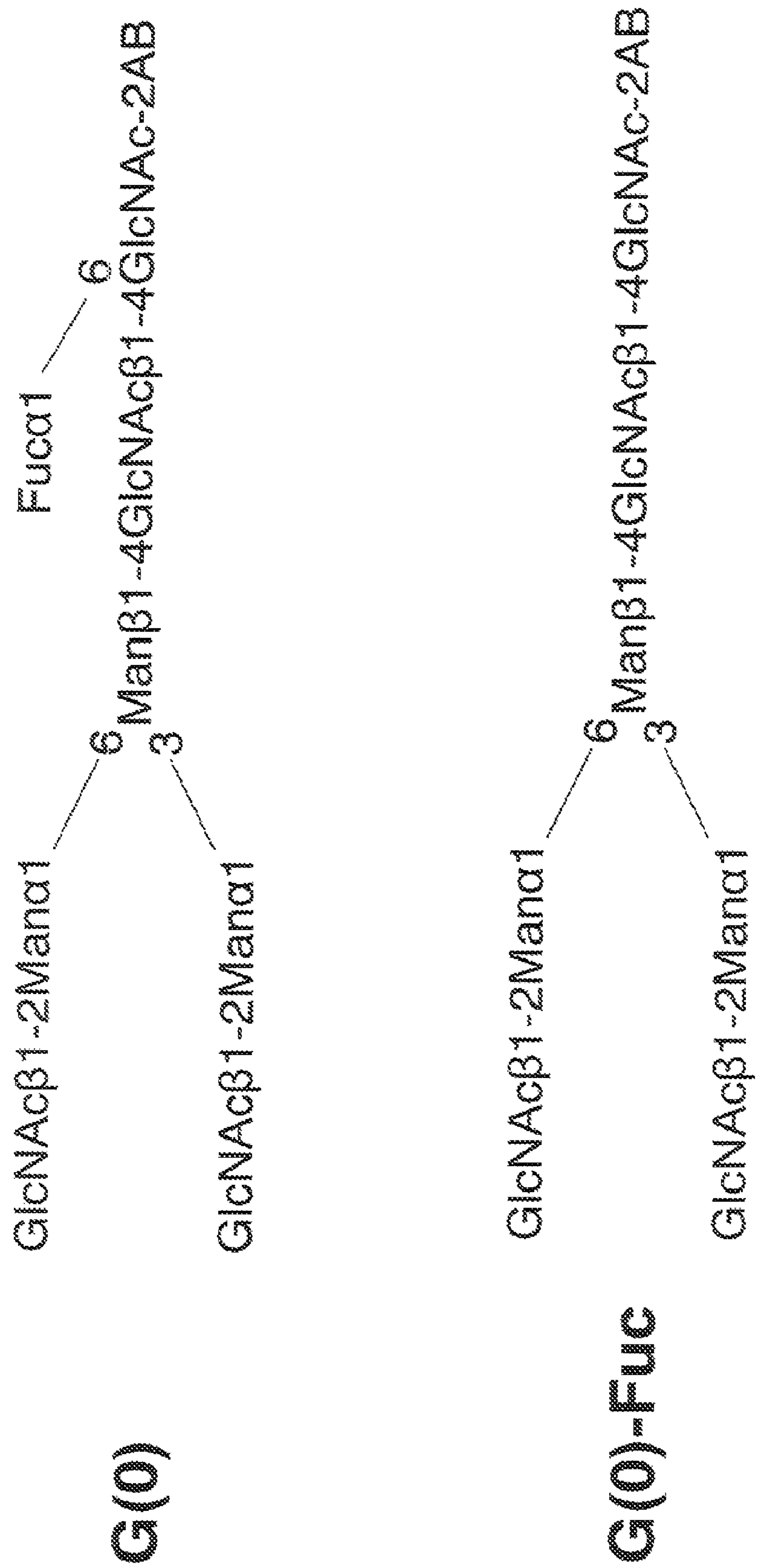
FIG. 6 shows the predicted structures for the G(0) and G(0)-Fuc peaks shown in FIG. 5.

TSKgel Amide-80), and the chromatograms were compared. In the antibodies produced by the CHO cells, the main component is G(0), and G(0)-Fuc accounts for about 4% of the peak area. On the other hand, in the antibodies produced by the FT-KO cells, G(0)-Fuc is the main component, and is present at not less than 90% of the peak area in each of the cell lines (FIG. 5 and Table 2). FIG. 6 shows the putative structures for peaks G(0) and G(0)-Fuc.

TABLE 2

Relative ratio of sugar chains estimated from normal phase HPLC analysis of agalactosyl 2-AB sugar chains

| Sugar chain | CHO | FT-KO-a | FT-KO-b | FT-KO-c |
|---|---|---|---|---|
| G(0)-Fuc | 4.0% | 92.4% | 92.5% | 93.2% |
| G(0) | 96.0% | 7.6% | 7.5% | 6.8% |

Example 9

Thermal Stability Analysis of Humanized Anti-GPC3 Antibody Produced by FT-KO Cells 1. Preparation of Sample Solution for DSC Measurement The external dialysis solution was 20 mol/L sodium acetate buffer (pH 6.0) containing 200 mmol/L sodium chloride. A dialysis membrane filled with 700 μg equivalents of antibody solution was dialyzed by immersing in the external dialysis solution overnight to prepare a sample solution.

2. Measurement of Thermal Degradation Temperature by DSC

Figure 7:
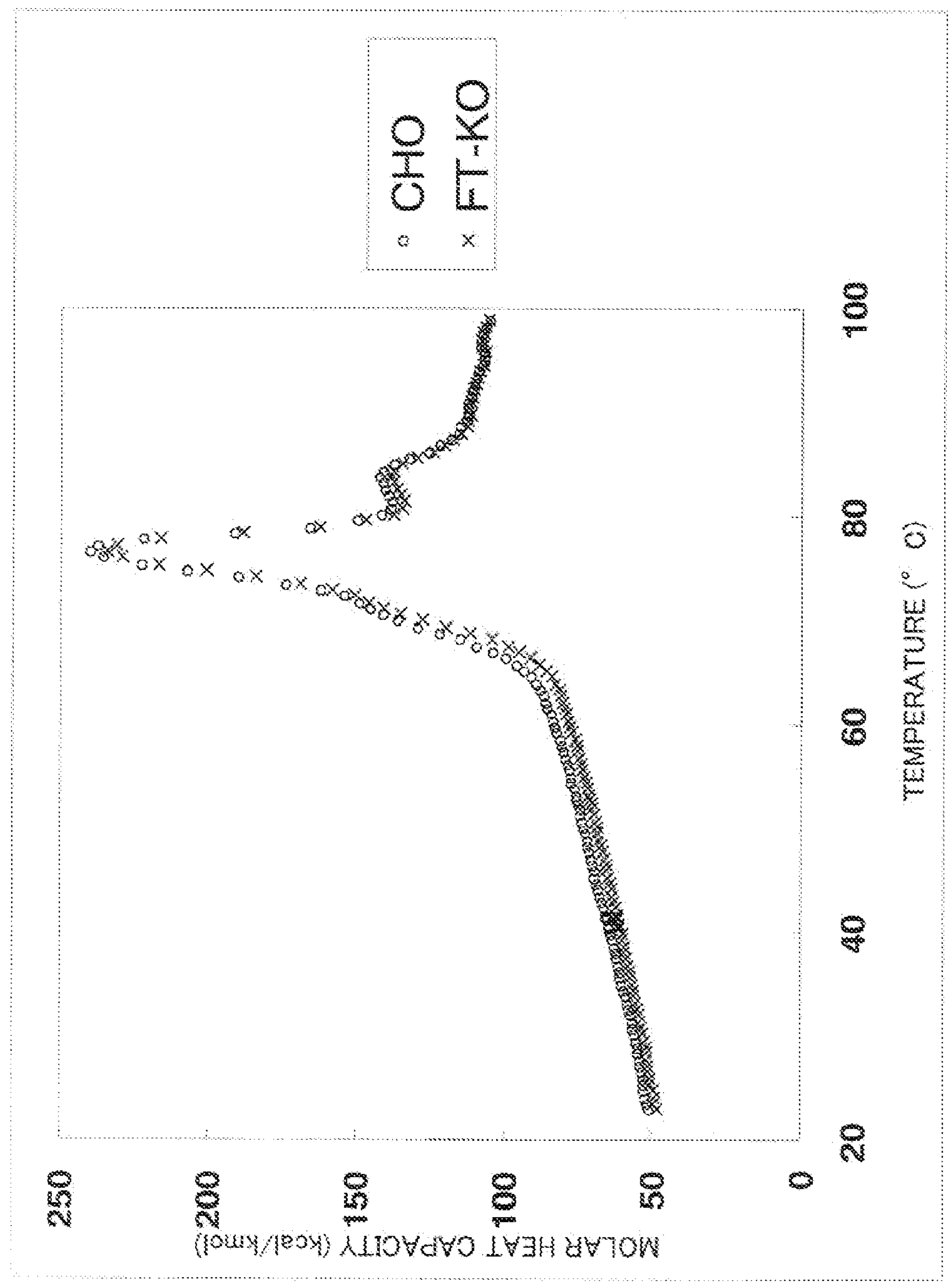
FIG. 7 shows a differential scanning calorimetry (DSC) measurement plot for the antibodies produced by FT-KO cells (x) and by CHO cells (o).

After both the sample solution and reference solution (external dialysis solution) were thoroughly degassed, they were each placed in the calorimeter and thermally equilibrated at 20° C. Next DSC measurement was carried out from 20° C. to 100° C. at a scan rate of approximately 1 K/min. The result is represented by the tip of the degradation peak as a function of temperature (FIG. 7). The thermal degradation temperature of the antibodies produced by CHO cells and the antibodies produced by FT-KO cells were found to be equivalent.

Reference Example 1

Humanization of GC33

Antibody sequence data were obtained from the publicly disclosed Kabat Database that is located at ebi.ac.uk/pub/databases/kabat/ and the ImMunoGeneTics Database (IMGT), and the H chain variable region and L chain variable region were separately subjected to a homology search. It was found that the H chain variable region has a high level of homology with DN13 (Smithson et al., Mol. Immunol. 1999; 36: 113-124). It was also found that the L chain variable region has a high level of homology with the Homo sapiens IGK mRNA for immunoglobulin kappa light chain VLJ region, partial cds, clone:K64 of Accession Number AB064105. The signal sequence of Accession Number S40357, which has a high level of homology with AB064105, was used as the L chain signal sequence. Then the CDR was grafted to the FR of these antibodies to prepare a humanized antibody.

More specifically, synthetic oligo-DNAs of approximately 50 base were designed in such a manner that approximately 20 bases of them were hybridized each other, and these synthetic oligo-DNAs were was assembled by PCR to prepare a gene encoding each variable region. They were digested at the HindIII sequence inserted at the terminus on the 5' end of the synthetic oligo-DNA and the BamHI sequence inserted at the terminus on the 3' end of the synthetic oligo-DNA, and the synthetic oligo-DNA was cloned into an expression vector HEFgγ1 where the human IgGb1 constant region was cloned, or to the expression vector HEFgκ where the human κ-chain constant region was cloned (Sato et al., Mol. Immunol., 1994; 371-381). The H chain and L chain of the humanized GC33 constructed as above were each designated ver.a. The humanized GC33 (ver.a/ver.a) wherein both the H chain and L chain were ver.a had lower binding activity than an antibody with the mouse GC33 variable regions (mouse/mouse). Chimeric antibodies were prepared by combining mouse GC33 sequences and ver.a sequences for the H chains and L chains (mouse/ver.a, ver.a/mouse), and the binding activity was evaluated. Lower binding activity was found with ver.a/mouse antibody, indicating that the decrease in binding activity is due to amino acid replacement was attributed to the H chain. Then modified H chains designated ver.c, ver.f, ver.h, ver.i, ver.j, and ver.k were prepared. All humanized GC33 antibodies exhibited the same level of binding activity as the chimeric antibody having mouse GC33 variable regions. The nucleotide sequences of the humanized GC33H chain variable regions ver.a, ver.c, ver.f, ver.h, ver.i, ver.j, and ver.k are shown in SEQ ID NOS:74, 75, 76, 77, 78, 79, and 80, and the amino acid sequences thereof are shown in SEQ ID NOS: 81, 82, 83, 84, 85, 86, and 87, respectively. The nucleotide sequence of the humanized GC33 L chain variable region ver.a is shown in SEQ ID NO: 88, and the amino acid sequence thereof is shown in SEQ ID NO: 89, respectively. In the humanized GC33H chain variable regions ver.i, ver.j, and ver.k, the sixth glutamic acid was replaced by a glutamine. These antibodies exhibited markedly increased thermal stability.

Reference Example 2

Alteration of Humanized GC33 L Chain

With respect to protein deamidation, the reaction rate constant of deamidation was known to be dependent on the primary sequence. It is also known that Asn-Gly is particularly susceptible to deamidation (Rocinson et al., Proc. Natl. Acad. Sci. USA 2001; 98: 944-949). Because Asn 33 within CDR1 of the humanized GC33 L chain ver.a variable region of SEQ ID NO: 88 has the primary sequence Asn-Gly, this residue is predicted to be susceptible to deamidation.

To evaluate the effect of deamidation of Asn 33 on binding activity of the antibody, a modified antibody was prepared wherein Asn 33 was replaced with Asp. Quick Change Site-Directed Mutagenesis Kit (Stratagene) was used for introducing a point mutation. More specifically, 50 μL of reaction solution containing 125 ng of sense primer (CTT GTA CAC AGT GAC GGA AAC ACC TAT: SEQ ID NO: 124), 125 ng of antisense primer (ATA GGT GTT TCC GTC ACT GTG TAC AAG: SEQ ID NO: 125), 5 μL of 10× reaction buffer, 1 μL of dNTP mix, 10 ng of HEFgκ to which humanized GC33 L chain ver.a had been cloned, and 1 μL of Pfu Turbo DNA Polymerase was run through 12 cycles consisting of 30 sec at 95° C., 1 min at 55° C., and 9 min at 68° C. The reaction product was digested with the restriction enzyme DpnI for 2 h at 37° C., and introduced into XL1-Blue competent cells to obtain transformants. The variable region was cut out from the clones containing the correct mutation and cloned again into the expression vector HEFgκ. The expression vector HEFgy1 containing humanized GC33H chain ver.k was introduced into COS7 cells by using Fugene 6 (Roche). Culture medium supernatant was collected from the cells transiently expressing the modified antibody. The antibody concentration was quantitated by sandwich ELISA using anti-human IgG antibody, and binding activity of the modified antibody was evaluated by ELISA using a plate coated with a soluble GPC3 core protein. Binding activity was lost in the modified antibody (N33D) in which Asn 33 was replaced by Asp, suggesting that the binding activity is significantly affected by deamidation at Asn 33.

Deamidation of Asn 33 was reported to be suppressed by replacing Gly 34 with another amino acid residue (WO 03057881 A1). In accordance with that method, a series of modified antibodies were prepared by replacing G34 with 17 other amino acid residues except for Cys and Met using the Quick Chane Site-Directed Mutagenesis Kit to prepare G34A, G34D, G34E, G34F, G34H, G34N, G34P, G34Q, G34I, G34K, G34L, G34V, G34W, G34Y, G34R, G34S, and G34T. The binding activity of the antibodies was evaluated using culture supernatant of COS7 cells transiently expressing the antibodies. It was revealed that binding activity is maintained even if G34 is replaced with another amino acid residues other than Pro (G34P), and Val (G34V).

The amino acid sequences of the L chain CDR1 of the modified antibodies are represented by SEQ ID NO: 90 (G34A), SEQ ID NO: 91 (G34D), SEQ ID NO: 92 (G34E), SEQ ID NO: 93 (G34F), SEQ ID NO: 94 (G34H), SEQ ID NO: 95 (G34N), SEQ ID NO: 96 (G34T), SEQ ID NO: 97 (G34Q), SEQ ID NO; 98 (G34I), SEQ ID NO: 99 (G34K), SEQ ID NO: 100 (G34L), SEQ ID NO: 101 (G34S), SEQ ID NO: 102 (G34W), SEQ ID NO: 103 (G34Y), SEQ ID NO: 104 (G34R), SEQ ID NO: 105 (G34V), and SEQ ID NO: 106 (G34P), respectively. The amino acid sequences of the L chain variable regions of the modified antibodies are represented by SEQ ID NO: 107 (G34A), SEQ ID NO: 108 (G34D), SEQ ID NO: 109 (G34K), SEQ ID NO: 110 (G34F), SEQ ID NO: 111 (G34H), SEQ ID NO: 112 (G34N), SEQ ID NO: 113 (G34T), SEQ ID NO: 114 (G34Q), SEQ ID NO: 115 (G34I), SEQ ID NO: 116 (G34K). SEQ ID NO: 117 (G34L), SEQ ID NO: 118 (G34S), SEQ ID NO: 119 (G34W), SEQ ID NO: 120 (G34Y), SEQ ID NO: 121 (G34R), SEQ ID NO: 122 (G34V), and SEQ ID NO: 123 (G34P), respectively.

Reference Example 3

Destruction of Fucose Transporter Gene in CHO Cells

1. Construction of Targeting Vector (1) Preparation of KO1 Vector

The hygromycin resistance gene (Hygr) was constructed by PCR with Hyg5-BH and Hyg3-NT primers from pcDNA3.1/Hygro (Invitrogen), which has a sequence identical to the 5' portion of the fucose transporter gene start codon by attaching a BamHI site and TGCGC sequence to the 5' portion of the start codon and a NotI site added to the 31 portion containing the region up to the SV40 polyA addition signal, and the Hygr fragment was cut off.

Forward Primer

```
Hyg5-BH
                                    (SEQ ID NO: 128)
5'-GGA TCC TGC GCA TGA AAA AGC CTG AAC TCA CC-3'
```

Reverse Primer

```
Hyg3-NT
                                    (SEQ ID NO: 129)
5'-GCG GCC GCC TAT TCC TTT GCC CTC GGA CG-3'
```

The fucose transporter targeting vector ver.1 (hereinafter designated the KO1 vector) was constructed by inserting the 51 portion of the fucose transporter (from the SmaI at base No. 2780 to the BamHI at base No. 4323 of the nucleotide sequence shown in SEQ ID NO: 126), the 3' portion (from base No. 4284 to the SacI at base No. 10934), and an Hygr fragment into pMC1DT-A vector (Yagi T, Proc. Natl. Acad. Sci. USA, Vol. 87, p. 9918-9922, 1990). The characteristic of the KO1 vector is that Hygr will be expressed from the fucose transporter promoter when homologous recombination takes place because no promoter is attached to the Hygr fragment. However, Hygr is not always expressed to the extent that resistance to hygromycin B is acquired if only one copy of the vector is inserted into a cell by homologous recombination. The KO1 vector was cleaved by NotI and introduced into the cell. It is expected that the fucose transporter will lose 41 base pairs of exon 1 including the start codon by introduction of the KO1 vector, which will result in the loss of its function.

(2) Preparation of pBSK-pgk-1-Hygr

The pBSK-pgk-1 vector was prepared by cutting off the mouse pgk-1 gene promoter from pKJ2 vector (Popo H, Biochemical Genetics, Vol. 28, p. 299-308, 1990) with EcoRI-PstI, and cloning it into the EcoRI-PstI site of pBluescript (Stratagene). By PCR with the Hyg5-AV and Hyg3-BH primers from pcDNA3.1/Hygro, an EcoT22I site and Kozak sequence were attached to the 5' portion of Hygr, and a BamHI site was added to the 3' portion containing the region up to the SV40 poly A addition signal, and then the Hygr fragment was cut off.

Forward Primer

```
Hyg5-AV
                                       (SEQ ID NO: 130)
5'-ATG CAT GCC ACC ATG AAA AAG CCT GAA CTC ACC -3'
```

Reverse Primer

```
Hyg3-BH
                                    (SEQ ID NO: 131)
5'-GGA TCC CAG GCT TTA CAC TTT ATG CTT C -3'
```

The pBSK-pgk-1-Hygr vector was prepared by inserting the Hygr (EcoT22I-BamHI) fragment into the PstI-BamHI site of pBSK-pgk-1.

(3) Preparation of the KO2 Vector

The fucose transporter targeting vector ver.2 (hereinafter designated the KO2 vector) was constructed by inserting the 5' portion of the fucose transporter (from the SmaI at base No. 2780 to the BamHI at base No. 4323 of the nucleotide sequence shown in SEQ ID NO: 126), the 3' portion (from base No. 4284 to the SacI at base No. 10934), and pgk-1Hygr fragment into pMC1DT-A vector. Unlike the KO1 vector, KO2 vector will confer resistance to hygromycin B even if only one copy of the vector is inserted by homologous recombination because the pgk-1 gene promoter is attached to Hygr. The KO2 vector was cleaved by NotI and inserted into the cells. It is expected that the fucose transporter will lose 46 base pairs of exon 1 including the start codon by the introduction of the KO2 vector, which will result in the loss of its function.

(4) Preparation of pBSK-pgk-1-Puror

The pBSK-pgk-1-Puror vector was prepared by cleaving pPUR vector (BD Biosciences) with PstI and BamHI, and inserting the digested fragment (Puror) into the PstI-BamHI site of pBSK-pgk-1.

(5) Preparation of the KO3 Vector

The fucose transporter targeting vector ver.3 (hereinafter designated the KO3 vector) was constructed by inserting the 5' portion of the fucose transporter (from the SmaI at base No. 2780 to the BamHI at base No. 4323 of the nucleotide sequence shown in SEQ ID NO: 126), the 3' portion (from base No. 4284 to the SacI at base No. 10934), and pgk-1-Puror fragment into pMC1DT-A vector. In addition, a sequence for binding with the primer for screening shown below was attached to the 3' end of pgk-1-Puror. The KO3 vector was cleaved by NotI and inserted into the cells. It is expected that the fucose transporter will lose 46 base pairs of exon 1 including the start codon by the introduction of the KO3 vector, which will result in the loss of its function.

Reverse Primer

```
                                        (SEQ ID NO: 132)
RSGR-A 5'-GCT GTC TGG AGT ACT GTG CAT CTG C -3'
```

The above three species of targeting vectors were used to knock out the fucose transporter gene.

2. Introduction of Vectors into CHO Cells

HT Supplement (100×) (Invitrogen Cat. No. 11067-030) and penicillin-streptomycin (Invitrogen Cat. No. 15140-122) were added to CHO-S-FMII HT (Invitrogen Cat. No. 12052-098), each at a volume of 1/100 with respect to the volume of CHO-S-SFMII HT. CHO DXB11 cells were subcultured in the culture medium (hereinafter designated SFMII(+)), and this SFMII(+) medium also used for culturing the cells after gene transfer. The CHO cells were suspended in Dulbecco phosphate buffer (hereinafter designated PBS, Invitrogen Cat. No. 14190-144) at a concentration of $8\times10^6$ cells/0.8 mL. Then 30 μg of the targeting vector was added to the cell suspension, and the cell suspension was transferred to a Gene Pulser Cuvette (4 mm) (Bio-Rad, Cat. No. 1652088). After the cuvette was let stand on ice for 10 min, the vector was introduced into the cells by electroporation with a GENE-PULSER II (Bio-Rad, Code No. 340BR) at 1.5 kV and 25 μFD. After introduction of the vector, the cells were suspended in 200 mL of SFMII(+) medium and transferred to twenty 96-well flat bottomed plates (Iwaki, Cat. No. 1860-096) at 100 μL/well. The plates were incubated in a $CO_2$ incubator for 24 h at 37° C., and then the reagent was added.

3. Knockout Step 1

Either the KO1 or KO2 vector was introduced into the CHO cells, and after 24 h the cells were selected using hygromycin B (Invitrogen, Cat. No. 10687-010). Hygromycin B was dissolved in the SFMII(+) up to a concentration of 0.3 mg/mL and was added at 100 μL/well.

4. Screening for Homologous Recombinants by PCR (1) Preparation of PCR Sample

Screening for homologous recombinants was carried out by PCR. The CHO cells used in screening were cultured in 96-well plates. After the supernatant was removed, 50 μL/well of buffer for cytolysis was added, and the cells were first heated at 55° C. for 2 h and then 95° C. for 15 min to inactivate protease K to prepare PCR template. The buffer for cytolysis consisted of 5 μL of 10×LA buffer II (Takara Bio Inc., LA Taq added), 2.5 μL of 10% NP-40 (Roche, Cat. No. 1 332 473), 4 μL of proteinase K (20 mg/mL, Takara Bio, Inc. Cat. No. 9033), and 38.5 μL of distilled water (Nacalai Tesque Cat. No. 36421-35) per well.

(2) PCR Conditions

PCR reaction mixture contained 1 μL of the above PCR sample, 5 μL of 10×LA buffer II, 5 μL of $MgCl_2$ (25 mM), 5 μL of dNTP (2.5 mM), 2 μL of primer (10 μM each), 0.5 μL of La Taq (5 IU/μL, Cat. No. RR002B) and 29.5 μL of distilled water (50 μL in total). For screening of cells containing the KO vector, TP-F4 and THygro-R1 were used as PCR primers, and for screening of cells containing the KO2 vector, TP-F4 and THygro-F1 were used as PCR primers.

PCR conditions for the cells containing the KO1 vector consisted of preheating at 95° C. for 1 min, conducting 40 cycles of the amplification cycle of 30 sec at 95° C., 30 sec at 60° C., and 2 min at 60° C., and then reheating at 72° C. for 7 min. PCR conditions for the cells containing the KO2 vector consisted of preheating at 95° C. for 1 min, 40 cycles of the amplification cycle of 30 sec at 95° C. and 3 min at 70° C., and then reheating at 70° C. for 7 min.

The primers used are listed below. In cell samples wherein homologous recombination occurred with the KO1 vector or the KO2 vector, DNA of approximately 1.6 kb or 2.0 kb will be amplified, respectively. The primer TP-F4 was designed for the 5' genome region of the fucose transporter outside of the vector, and THygro-F1 and THygro-R1 were designed for the Hygr gene inside of the vector.

Forward Primer (KO1, KO2)

```
                                        (SEQ ID NO: 133)
TP-F4 5'-GGA ATG CAG CTT CCT CAA GGG ACT CGC-3'
```

Reverse Primer (KO1)

```
THygro-R1
                                        (SEQ ID NO: 134)
5'-TGC ATC AGG TCG GAG ACG CTG TCG AAC-3'
```

Reverse Primer (KO2)

```
THygro-F1
                                        (SEQ ID NO: 135)
5'-GCA CTC GTC CGA GGG CAA AGG AAT AGC-3'
```

5. PCR Screening Results

A total of 918 cells containing the KO1 vector were analyzed, and 1 cell was appeared to be a homologous recombinant (homologous recombination rate: approximately 0.1%). A total of 537 cells containing the KO2 vector were analyzed and 17 cells were appeared to be homologous recombinants (homologous recombination rate: approximately 3.2%).

6. Southern Blot Analysis

Homologous recombination was further confirmed by Southern blot. A total of 10 μg of genomic DNA was prepared from the cultured cells by the standard method to be analyzed in Southern blotting. PCR was conducted using the two primers listed below to prepare a 387 bp probe corresponding to the region of base Nose. 2113 to 2500 of the nucleotide sequence shown in SEQ ID NO: 126, which was used in Southern blotting. The genomic DNA was cleaved by BglII.

Forward Primer

```
                                    (SEQ ID NO: 136)
Bgl-F: 5'-TGT GCT GGG AAT TGA ACC CAG GAC -3'
```

Reverse Primer

```
                                    (SEQ ID NO: 137)
Bgl-R: 5'-CTA CTT GTC TGT GCT TTC TTC C -3'
```

As a result of cleavage with BglII, the blot will show a band of approximately 30 kb from the fucose transporter chromosome, approximately 4.6 kb from the chromosome wherein homologous recombination with the KO1 vector occurred, and approximately 5.0 kb from the chromosome wherein homologous recombination with the KO2 vector occurred. The experiment comprised 1 cell from homologous recombination with the KO1 vector and 7 cells from homologous recombination with the KO2 vector. The only cell obtained from the homologous recombination with the KO1 vector was first designated 5C1, but later analysis revealed that this cell consisted of multiple cell populations. Therefore the cells were cloned by limiting dilution before used in the experiment. One of the cells obtained with the KO2 vector was designated 6E2.

7. Knockout Step 2

The three vectors were used to establish cell lines completely defective of fucose transporter gene from the cells wherein homologous recombination with the KO1 and KO2 vectors took place. The combinations of vectors and cells was as follows: Method 1 combined the KO2 vector and 5C1 cells (KO1), Method 2 combined the KO2 vector and 6E2 cells (KO2), and Method 3 combined the KO3 vector and 6E2 cells (KO2). Each vector was introduced into the appropriate cells, and after 24 h selection was started using hygromycin B and puromycin (Nacalai Tesque, Cat. No. 29455-12). The final concentration of hygromycin B was set to 1 mg/mL in Method 1, and 7 mg/mL in Method 2. In Method 3 hygromycin B was added at a final concentration of 0.15 mg/mL and puromycin at a final concentration of 8 μg/ml.

8. Screening for Homologous Recombinants by PCR

For screening of cells from Method 1, PCR was carried out to detect cells having homologous recombination with both KO1 and KO2 vectors. For screening of cells from Method 2 the following PCR primers were designed: TPS-F1 was configured in the region from base Nos. 3924 to 3950 of SEQ ID NO: 126, and SHygro-R1 was configured in the region from base Nos. 4248 to 4274. These primers will amplify 350 bp of the fucose transporter gene region containing a deletion due to the KO2 vector. Therefore, in the PCR screening in Method 2, those dells providing no amplification product of 350 bp are considered to be completely lacking the fucose transporter gene. The PCR conditions consisted of preheating for 1 min at 95° C., 35 cycles of the amplification cycle of 30 sec at 95° C. and 1 min at 70° C., and reheating for 7 min at 70° C.

Forward Primer

```
                                        (SEQ ID NO: 138)
TPS-F1: 5'-CTC GAC TCG TCC CTA TTA GGC AAC AGC -3'
```

Reverse Primer

```
SHygro-R1:
                                    (SEQ ID NO: 139)
5'-TCA GAG GCA GTG GAG CCT CCA GTC AGC -3'
```

For Method 3, TP-F4 was used as the forward primer and RSGR-A was used as the reverse primer. The PCR conditions consisted of preheating for 1 min at 95° C., 35 cycles of the amplification cycle of 30 sec at 95° C., 30 sec at 60° C., and 2 min at 72° C., and reheating for 7 min at 72° C. In the sample of cells having homologous recombination with the KO3 vector, DNA of approximately 1.6 kb will be amplified. This PCR procedure will detect those cells having homologous recombination with the KO3 vector and also those still having homologous recombination with the KO2 vector.

9. PCR Screening Results

In Method 1, a total of 616 cells were analyzed, and 18 cells were appeared to be homologous recombinants (homologous recombination rate: 2.9%). In Method 2, a total of 524 cells were analyzed, and 2 cells were appeared to be homologous recombinants (homologous recombination rate: 0.4%). In addition, in Method 3, a total of 382 cells were analyzed, and 7 cells were appeared to be homologous recombinants (homologous recombination rate: 1.8%).

10. Southern Blot Analysis

Southern blotting was carried out according to the method described above. Among the cells analyzed, 1 cell completely lacking the fucose transporter gene was found. In knockout step 1, the analysis results of PCR and Southern blotting were consistent, but not in knockout step 2. Possible causes are as follows: 1. In Method 1 cells having homologous recombination independently with either KO1 or KO2 were mixed together; 2. The fucose transporter gene is present not as one pair (2 genes) but as multiple pairs (or not less than 3 genes); and 3. During the culture of the cell lines established in the knockout step 1, the copy number of the fucose transporter gene remaining in the subcultured cells increased.

11. Analysis of Fucose Expression

Fucose expression was analyzed by PCR in 26 cells found to be homologous recombinants. A total of $1\times10^6$ cells were stained on ice for 1 h with 100 μL of PBS containing 5 μg/mL of *Lens culinaris* Agglutinin, FITC conjugate (Vector Laboratories, Cat. No. FL-1041) 2.5% FBS, and 0.02% sodium azide (hereinafter designated as FACS solution). Then the cells were rinsed 3 times with FACS solution and analyzed with FACSCalibur (Becton Dickinson). The results clearly showed that fucose expression is decreased only in the cells found to be completely lacking the fucose transporter gene in the Southern blot analysis.

The above results have revealed the following:

From the fact that only one cell out of 616 cells screened has complete deletion of the fucose transporter gene, the frequency of homologous recombination was very low at approximately 0.16%. As noted above, there are several possible reasons why the results of PCR and Southern blot analysis in knockout step 2 was not consistent. However, the cell lines obtained in Method 3 may not comprise a mixture of cells having homologous recombination independently with the KO2 and KO3 vectors, because selection was made using two types of drugs. In addition, it is unlikely that all of the other cell lines having homologous recombination by PCR comprise multiple cell populations. As noted above, if there are 3 or more fucose transporter genes present, targeting of the gene in cells would be particularly difficult. Homologous recombinants could be obtained only by using a vector such as the KO1 vector where Hyger is hardly expressed and by screening a large number of cells.

The invention claimed is:

1. A method for producing an anti-glypican 3 antibody with a modified sugar chain component, the method comprising:

(a) providing a cell expressing a nucleic acid encoding an anti-glypican 3 antibody, wherein the cell is a mutant cell that has a reduced capability of adding fucose to sugar chains as compared to a corresponding wild type cell; and (b) culturing the mutant cell, thereby producing the anti-glypican 3 antibody with a modified sugar chain component, wherein the anti-glypican 3 antibody comprises a heavy chain variable region comprising an amino acid sequence selected from the group consisting of SEQ ID NO:81, SEQ ID NO:82, SEQ ID NO:83, SEQ ID NO:84, SEQ ID NO:85, SEQ ID NO:86, and SEQ ID NO:87.

2. A method for producing an anti-glypican 3 antibody with a modified sugar chain component, the method comprising:

(a) providing a cell expressing a nucleic acid encoding an anti-glypican 3 antibody, wherein the cell is a mutant cell that has a reduced capability of adding fucose to sugar chains as compared to a corresponding wild type cell; and (b) culturing the mutant cell, thereby producing the anti-glypican 3 antibody with a modified sugar chain component, wherein the anti-glypican 3 antibody comprises a light chain variable region comprising the amino acid sequence of SEQ ID NO:109.

3. The method of claim 1, wherein the mutant cell lacks a fucose transporter.

4. The method of claim 2, wherein the mutant cell lacks a fucose transporter.

5. The method of claim 1, further comprising introducing the nucleic acid encoding the anti-glypican 3 antibody into the mutant cell.

6. The method of claim 2, further comprising introducing the nucleic acid encoding the anti-glypican 3 antibody into the mutant cell.

7. The method of claim 1, further comprising collecting and purifying the antibody.

8. The method of claim 2, further comprising collecting and purifying the antibody.

* * * * *

SEQUENCE LISTING

<160> NUMBER OF SEQ ID NOS: 139

<210> SEQ ID NO 1
<211> LENGTH: 1743
<212> TYPE: DNA
<213> ORGANISM: Homo sapiens

<400> SEQUENCE: 1

```
atggccggga ccgtgcgcac cgcgtgcttg gtggtggcga tgctgctcag cttggacttc     60

ccgggacagg cgcagccccc gccgccgccg ccggacgcca cctgtcacca agtccgctcc    120

ttcttccaga gactgcagcc cggactcaag tgggtgccag aaactcccgt gccaggatca    180

gatttgcaag tatgtctccc taagggccca acatgctgct caagaaagat ggaagaaaaa    240

taccaactaa cagcacgatt gaacatggaa cagctgcttc agtctgcaag tatggagctc    300

aagttcttaa ttattcagaa tgctgcggtt ttccaagagg cctttgaaat tgttgttcgc    360

catgccaaga actacaccaa tgccatgttc aagaacaact acccaagcct gactccacaa    420

gcttttgagt ttgtgggtga atttttcaca gatgtgtctc tctacatctt gggttctgac    480

atcaatgtag atgacatggt caatgaattg tttgacagcc tgtttccagt catctatacc    540

cagctaatga acccaggcct gcctgattca gccttggaca tcaatgagtg cctccgagga    600

gcaagacgtg acctgaaagt atttgggaat ttccccaagc ttattatgac ccaggtttcc    660

aagtcactgc aagtcactag gatcttcctt caggctctga atcttggaat tgaagtgatc    720

aacacaactg atcacctgaa gttcagtaag gactgtggcc gaatgctcac cagaatgtgg    780

tactgctctt actgccaggg actgatgatg gttaaaccct gtggcggtta ctgcaatgtg    840

gtcatgcaag gctgtatggc aggtgtggtg gagattgaca agtactggag agaatacatt    900

ctgtcccttg aagaacttgt gaatggcatg tacagaatct atgacatgga gaacgtactg    960

cttggtctct tttcaacaat ccatgattct atccagtatg tccagaagaa tgcaggaaag   1020

ctgaccacca ctattggcaa gttatgtgcc cattctcaac aacgccaata tagatctgct   1080

tattatcctg aagatctctt tattgacaag aaagtattaa aagttgctca tgtagaacat   1140

gaagaaacct tatccagccg aagaagggaa ctaattcaga agttgaagtc tttcatcagc   1200

ttctatagtg ctttgcctgg ctacatctgc agccatagcc ctgtggcgga aaacgacacc   1260

ctttgctgga atggacaaga actcgtggag agatacagcc aaaaggcagc aaggaatgga   1320

atgaaaaacc agttcaatct ccatgagctg aaaatgaagg gccctgagcc agtggtcagt   1380

caaattattg acaaactgaa gcacattaac cagctcctga gaaccatgtc tatgcccaaa   1440

ggtagagttc tggataaaaa cctggatgag gaagggtttg aaagtggaga ctgcggtgat   1500

gatgaagatg agtgcattgg aggctctggt gatggaatga taaaagtgaa gaatcagctc   1560

cgcttccttg cagaactggc ctatgatctg gatgtggatg atgcgcctgg aaacagtcag   1620

caggcaactc cgaaggacaa cgagataagc acctttcaca acctcgggaa cgttcattcc   1680

ccgctgaagc ttctcaccag catggccatc tcggtggtgt gcttcttctt cctggtgcac   1740

tga                                                                 1743
```

<210> SEQ ID NO 2
<211> LENGTH: 580
<212> TYPE: PRT
<213> ORGANISM: Homo sapiens

<400> SEQUENCE: 2

-continued

```
Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Pro Asp
            20                  25                  30

Ala Thr Cys His Gln Val Arg Ser Phe Phe Gln Arg Leu Gln Pro Gly
        35                  40                  45

Leu Lys Trp Val Pro Glu Thr Pro Val Pro Gly Ser Asp Leu Gln Val
    50                  55                  60

Cys Leu Pro Lys Gly Pro Thr Cys Cys Ser Arg Lys Met Glu Glu Lys
65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
            100                 105                 110

Glu Ala Phe Glu Ile Val Val Arg His Ala Lys Asn Tyr Thr Asn Ala
        115                 120                 125

Met Phe Lys Asn Asn Tyr Pro Ser Leu Thr Pro Gln Ala Phe Glu Phe
    130                 135                 140

Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
                165                 170                 175

Val Ile Tyr Thr Gln Leu Met Asn Pro Gly Leu Pro Asp Ser Ala Leu
            180                 185                 190

Asp Ile Asn Glu Cys Leu Arg Gly Ala Arg Arg Asp Leu Lys Val Phe
        195                 200                 205

Gly Asn Phe Pro Lys Leu Ile Met Thr Gln Val Ser Lys Ser Leu Gln
    210                 215                 220

Val Thr Arg Ile Phe Leu Gln Ala Leu Asn Leu Gly Ile Glu Val Ile
225                 230                 235                 240

Asn Thr Thr Asp His Leu Lys Phe Ser Lys Asp Cys Gly Arg Met Leu
                245                 250                 255

Thr Arg Met Trp Tyr Cys Ser Tyr Cys Gln Gly Leu Met Met Val Lys
            260                 265                 270

Pro Cys Gly Gly Tyr Cys Asn Val Val Met Gln Gly Cys Met Ala Gly
        275                 280                 285

Val Val Glu Ile Asp Lys Tyr Trp Arg Glu Tyr Ile Leu Ser Leu Glu
    290                 295                 300

Glu Leu Val Asn Gly Met Tyr Arg Ile Tyr Asp Met Glu Asn Val Leu
305                 310                 315                 320

Leu Gly Leu Phe Ser Thr Ile His Asp Ser Ile Gln Tyr Val Gln Lys
                325                 330                 335

Asn Ala Gly Lys Leu Thr Thr Thr Ile Gly Lys Leu Cys Ala His Ser
            340                 345                 350

Gln Gln Arg Gln Tyr Arg Ser Ala Tyr Tyr Pro Glu Asp Leu Phe Ile
        355                 360                 365

Asp Lys Lys Val Leu Lys Val Ala His Val Glu His Glu Glu Thr Leu
    370                 375                 380

Ser Ser Arg Arg Arg Glu Leu Ile Gln Lys Leu Lys Ser Phe Ile Ser
385                 390                 395                 400

Phe Tyr Ser Ala Leu Pro Gly Tyr Ile Cys Ser His Ser Pro Val Ala
                405                 410                 415
```

-continued

Glu Asn Asp Thr Leu Cys Trp Asn Gly Gln Glu Leu Val Glu Arg Tyr
420 425 430

Ser Gln Lys Ala Ala Arg Asn Gly Met Lys Asn Gln Phe Asn Leu His
435 440 445

Glu Leu Lys Met Lys Gly Pro Glu Pro Val Val Ser Gln Ile Ile Asp
450 455 460

Lys Leu Lys His Ile Asn Gln Leu Leu Arg Thr Met Ser Met Pro Lys
465 470 475 480

Gly Arg Val Leu Asp Lys Asn Leu Asp Glu Glu Gly Phe Glu Ser Gly
485 490 495

Asp Cys Gly Asp Asp Glu Asp Glu Cys Ile Gly Gly Ser Gly Asp Gly
500 505 510

Met Ile Lys Val Lys Asn Gln Leu Arg Phe Leu Ala Glu Leu Ala Tyr
515 520 525

Asp Leu Asp Val Asp Asp Ala Pro Gly Asn Ser Gln Gln Ala Thr Pro
530 535 540

Lys Asp Asn Glu Ile Ser Thr Phe His Asn Leu Gly Asn Val His Ser
545 550 555 560

Pro Leu Lys Leu Leu Thr Ser Met Ala Ile Ser Val Val Cys Phe Phe
565 570 575

Phe Leu Val His
580

<210> SEQ ID NO 3
<211> LENGTH: 115
<212> TYPE: PRT
<213> ORGANISM: Mus musculus

<400> SEQUENCE: 3

Gln Val Gln Leu Gln Gln Ser Gly Ala Glu Leu Val Arg Pro Gly Ala
1 5 10 15

Ser Val Lys Leu Ser Cys Lys Ala Ser Gly Tyr Thr Phe Thr Asp Tyr
20 25 30

Glu Met His Trp Val Lys Gln Thr Pro Val His Gly Leu Lys Trp Ile
35 40 45

Gly Ala Leu Asp Pro Lys Thr Gly Asp Thr Ala Tyr Ser Gln Lys Phe
50 55 60

Lys Gly Lys Ala Thr Leu Thr Ala Asp Lys Ser Ser Ser Thr Ala Tyr
65 70 75 80

Met Glu Leu Arg Ser Leu Thr Ser Glu Asp Ser Ala Val Tyr Tyr Cys
85 90 95

Thr Arg Phe Tyr Ser Tyr Thr Tyr Trp Gly Gln Gly Thr Leu Val Thr
100 105 110

Val Ser Ala
115

<210> SEQ ID NO 4
<211> LENGTH: 112
<212> TYPE: PRT
<213> ORGANISM: Mus musculus

<400> SEQUENCE: 4

Asp Val Val Met Thr Gln Thr Pro Leu Ser Leu Pro Val Ser Leu Gly
1 5 10 15

Asp Gln Ala Ser Ile Ser Cys Arg Ser Ser Gln Ser Leu Val His Ser
20 25 30

-continued

```
Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr His Val Pro Pro Thr Phe Gly Ser Gly Thr Lys Leu Glu Ile Lys
            100                 105                 110


<210> SEQ ID NO 5
<211> LENGTH: 5
<212> TYPE: PRT
<213> ORGANISM: Mus musculus

<400> SEQUENCE: 5

Asn Tyr Ala Met Ser
1               5


<210> SEQ ID NO 6
<211> LENGTH: 17
<212> TYPE: PRT
<213> ORGANISM: Mus musculus

<400> SEQUENCE: 6

Ala Ile Asn Asn Asn Gly Asp Asp Thr Tyr Tyr Leu Asp Thr Val Lys
1               5                   10                  15

Asp


<210> SEQ ID NO 7
<211> LENGTH: 5
<212> TYPE: PRT
<213> ORGANISM: Mus musculus

<400> SEQUENCE: 7

Gln Gly Gly Ala Tyr
1               5


<210> SEQ ID NO 8
<211> LENGTH: 7
<212> TYPE: PRT
<213> ORGANISM: Mus musculus

<400> SEQUENCE: 8

Thr Tyr Gly Met Gly Val Gly
1               5


<210> SEQ ID NO 9
<211> LENGTH: 16
<212> TYPE: PRT
<213> ORGANISM: Mus musculus

<400> SEQUENCE: 9

Asn Ile Trp Trp Tyr Asp Ala Lys Tyr Tyr Asn Ser Asp Leu Lys Ser
1               5                   10                  15


<210> SEQ ID NO 10
<211> LENGTH: 8
<212> TYPE: PRT
<213> ORGANISM: Mus musculus

<400> SEQUENCE: 10
```

Met Gly Leu Ala Trp Phe Ala Tyr
1 5

<210> SEQ ID NO 11
<211> LENGTH: 7
<212> TYPE: PRT
<213> ORGANISM: Mus musculus

<400> SEQUENCE: 11

Ile Tyr Gly Met Gly Val Gly
1 5

<210> SEQ ID NO 12
<211> LENGTH: 16
<212> TYPE: PRT
<213> ORGANISM: Mus musculus

<400> SEQUENCE: 12

Asn Ile Trp Trp Asn Asp Asp Lys Tyr Tyr Asn Ser Ala Leu Lys Ser
1 5 10 15

<210> SEQ ID NO 13
<211> LENGTH: 8
<212> TYPE: PRT
<213> ORGANISM: Mus musculus

<400> SEQUENCE: 13

Ile Gly Tyr Phe Tyr Phe Asp Tyr
1 5

<210> SEQ ID NO 14
<211> LENGTH: 5
<212> TYPE: PRT
<213> ORGANISM: Mus musculus

<400> SEQUENCE: 14

Gly Tyr Trp Met His
1 5

<210> SEQ ID NO 15
<211> LENGTH: 17
<212> TYPE: PRT
<213> ORGANISM: Mus musculus

<400> SEQUENCE: 15

Ala Ile Tyr Pro Gly Asn Ser Asp Thr Asn Tyr Asn Gln Lys Phe Lys
1 5 10 15

Gly

<210> SEQ ID NO 16
<211> LENGTH: 10
<212> TYPE: PRT
<213> ORGANISM: Mus musculus

<400> SEQUENCE: 16

Ser Gly Asp Leu Thr Gly Gly Leu Ala Tyr
1 5 10

<210> SEQ ID NO 17
<211> LENGTH: 5
<212> TYPE: PRT
<213> ORGANISM: Mus musculus

<400> SEQUENCE: 17

```
Ser Tyr Ala Met Ser
1               5


<210> SEQ ID NO 18
<211> LENGTH: 17
<212> TYPE: PRT
<213> ORGANISM: Mus musculus

<400> SEQUENCE: 18

Ala Ile Asn Ser Asn Gly Gly Thr Thr Tyr Tyr Pro Asp Thr Met Lys
1               5                   10                  15

Asp


<210> SEQ ID NO 19
<211> LENGTH: 13
<212> TYPE: PRT
<213> ORGANISM: Mus musculus

<400> SEQUENCE: 19

His Asn Gly Gly Tyr Glu Asn Tyr Gly Trp Phe Ala Tyr
1               5                   10


<210> SEQ ID NO 20
<211> LENGTH: 5
<212> TYPE: PRT
<213> ORGANISM: Mus musculus

<400> SEQUENCE: 20

Ser Tyr Trp Met His
1               5


<210> SEQ ID NO 21
<211> LENGTH: 17
<212> TYPE: PRT
<213> ORGANISM: Mus musculus

<400> SEQUENCE: 21

Glu Ile Asp Pro Ser Asp Ser Tyr Thr Tyr Tyr Asn Gln Lys Phe Arg
1               5                   10                  15

Gly


<210> SEQ ID NO 22
<211> LENGTH: 15
<212> TYPE: PRT
<213> ORGANISM: Mus musculus

<400> SEQUENCE: 22

Ser Asn Leu Gly Asp Gly His Tyr Arg Phe Pro Ala Phe Pro Tyr
1               5                   10                  15


<210> SEQ ID NO 23
<211> LENGTH: 17
<212> TYPE: PRT
<213> ORGANISM: Mus musculus

<400> SEQUENCE: 23

Thr Ile Asp Pro Ser Asp Ser Glu Thr His Tyr Asn Leu Gln Phe Lys
1               5                   10                  15

Asp


<210> SEQ ID NO 24
<211> LENGTH: 15
```

<212> TYPE: PRT
<213> ORGANISM: Mus musculus

<400> SEQUENCE: 24

Gly Ala Phe Tyr Ser Ser Tyr Ser Tyr Trp Ala Trp Phe Ala Tyr
1 5 10 15

<210> SEQ ID NO 25
<211> LENGTH: 5
<212> TYPE: PRT
<213> ORGANISM: Mus musculus

<400> SEQUENCE: 25

Asp Tyr Glu Met His
1 5

<210> SEQ ID NO 26
<211> LENGTH: 17
<212> TYPE: PRT
<213> ORGANISM: Mus musculus

<400> SEQUENCE: 26

Ala Leu Asp Pro Lys Thr Gly Asp Thr Ala Tyr Ser Gln Lys Phe Lys
1 5 10 15

Gly

<210> SEQ ID NO 27
<211> LENGTH: 6
<212> TYPE: PRT
<213> ORGANISM: Mus musculus

<400> SEQUENCE: 27

Phe Tyr Ser Tyr Thr Tyr
1 5

<210> SEQ ID NO 28
<211> LENGTH: 5
<212> TYPE: PRT
<213> ORGANISM: Mus musculus

<400> SEQUENCE: 28

Ile Asn Ala Met Asn
1 5

<210> SEQ ID NO 29
<211> LENGTH: 19
<212> TYPE: PRT
<213> ORGANISM: Mus musculus

<400> SEQUENCE: 29

Arg Ile Arg Ser Glu Ser Asn Asn Tyr Ala Thr Tyr Tyr Gly Asp Ser
1 5 10 15

Val Lys Asp

<210> SEQ ID NO 30
<211> LENGTH: 8
<212> TYPE: PRT
<213> ORGANISM: Mus musculus

<400> SEQUENCE: 30

Glu Val Thr Thr Ser Phe Ala Tyr
1 5

-continued

<210> SEQ ID NO 31
<211> LENGTH: 5
<212> TYPE: PRT
<213> ORGANISM: Mus musculus

<400> SEQUENCE: 31

Ala Ser Ala Met Asn
1               5

<210> SEQ ID NO 32
<211> LENGTH: 19
<212> TYPE: PRT
<213> ORGANISM: Mus musculus

<400> SEQUENCE: 32

Arg Ile Arg Ser Lys Ser Asn Asn Tyr Ala Ile Tyr Tyr Ala Asp Ser
1               5                   10                  15

Val Lys Asp

<210> SEQ ID NO 33
<211> LENGTH: 12
<212> TYPE: PRT
<213> ORGANISM: Mus musculus

<400> SEQUENCE: 33

Asp Pro Gly Tyr Tyr Gly Asn Pro Trp Phe Ala Tyr
1               5                   10

<210> SEQ ID NO 34
<211> LENGTH: 5
<212> TYPE: PRT
<213> ORGANISM: Mus musculus

<400> SEQUENCE: 34

Asp Tyr Ser Met His
1               5

<210> SEQ ID NO 35
<211> LENGTH: 17
<212> TYPE: PRT
<213> ORGANISM: Mus musculus

<400> SEQUENCE: 35

Trp Ile Asn Thr Glu Thr Gly Glu Pro Thr Tyr Ala Asp Asp Phe Lys
1               5                   10                  15

Gly

<210> SEQ ID NO 36
<211> LENGTH: 2
<212> TYPE: PRT
<213> ORGANISM: Mus musculus

<400> SEQUENCE: 36

Leu Tyr
1

<210> SEQ ID NO 37
<211> LENGTH: 16
<212> TYPE: PRT
<213> ORGANISM: Mus musculus

<400> SEQUENCE: 37

Asn Ile Trp Trp His Asp Asp Lys Tyr Tyr Asn Ser Ala Leu Lys Ser
1               5                   10                  15

<210> SEQ ID NO 38
<211> LENGTH: 14
<212> TYPE: PRT
<213> ORGANISM: Mus musculus

<400> SEQUENCE: 38

Ile Ala Pro Arg Tyr Asn Lys Tyr Glu Gly Phe Phe Ala Phe
1 5 10

<210> SEQ ID NO 39
<211> LENGTH: 16
<212> TYPE: PRT
<213> ORGANISM: Mus musculus

<400> SEQUENCE: 39

Lys Ser Ser Gln Ser Leu Leu Asp Ser Asp Gly Lys Thr Tyr Leu Asn
1 5 10 15

<210> SEQ ID NO 40
<211> LENGTH: 7
<212> TYPE: PRT
<213> ORGANISM: Mus musculus

<400> SEQUENCE: 40

Leu Val Ser Lys Leu Asp Ser
1 5

<210> SEQ ID NO 41
<211> LENGTH: 9
<212> TYPE: PRT
<213> ORGANISM: Mus musculus

<400> SEQUENCE: 41

Trp Gln Gly Thr His Phe Pro Leu Thr
1 5

<210> SEQ ID NO 42
<211> LENGTH: 11
<212> TYPE: PRT
<213> ORGANISM: Mus musculus

<400> SEQUENCE: 42

Lys Ala Ser Gln Asp Ile Asn Asn Tyr Leu Ser
1 5 10

<210> SEQ ID NO 43
<211> LENGTH: 7
<212> TYPE: PRT
<213> ORGANISM: Mus musculus

<400> SEQUENCE: 43

Arg Ala Asn Arg Leu Val Asp
1 5

<210> SEQ ID NO 44
<211> LENGTH: 10
<212> TYPE: PRT
<213> ORGANISM: Mus musculus

<400> SEQUENCE: 44

Leu Gln Cys Asp Glu Phe Pro Pro Trp Thr
1 5 10

<210> SEQ ID NO 45
<211> LENGTH: 16
<212> TYPE: PRT
<213> ORGANISM: Mus musculus

<400> SEQUENCE: 45

Arg Ser Ser Gln Ser Leu Val His Ser Asn Gly Asn Thr Tyr Leu His
1 5 10 15

<210> SEQ ID NO 46
<211> LENGTH: 7
<212> TYPE: PRT
<213> ORGANISM: Mus musculus

<400> SEQUENCE: 46

Lys Val Ser Asn Arg Phe Ser
1 5

<210> SEQ ID NO 47
<211> LENGTH: 9
<212> TYPE: PRT
<213> ORGANISM: Mus musculus

<400> SEQUENCE: 47

Ser Gln Ser Thr His Val Pro Trp Thr
1 5

<210> SEQ ID NO 48
<211> LENGTH: 16
<212> TYPE: PRT
<213> ORGANISM: Mus musculus

<400> SEQUENCE: 48

Arg Ser Ser Lys Ser Leu Leu His Ser Asn Gly Ile Thr Tyr Leu Tyr
1 5 10 15

<210> SEQ ID NO 49
<211> LENGTH: 7
<212> TYPE: PRT
<213> ORGANISM: Mus musculus

<400> SEQUENCE: 49

Gln Met Ser Asn Leu Ala Ser
1 5

<210> SEQ ID NO 50
<211> LENGTH: 9
<212> TYPE: PRT
<213> ORGANISM: Mus musculus

<400> SEQUENCE: 50

Ala Gln Asn Leu Glu Leu Pro Tyr Thr
1 5

<210> SEQ ID NO 51
<211> LENGTH: 11
<212> TYPE: PRT
<213> ORGANISM: Mus musculus

<400> SEQUENCE: 51

Lys Ala Ser Gln Asp Ile Asn Lys Asn Ile Ile
1 5 10

<210> SEQ ID NO 52
<211> LENGTH: 7

<212> TYPE: PRT
<213> ORGANISM: Mus musculus

<400> SEQUENCE: 52

Tyr Thr Ser Thr Leu Gln Pro
1               5

<210> SEQ ID NO 53
<211> LENGTH: 9
<212> TYPE: PRT
<213> ORGANISM: Mus musculus

<400> SEQUENCE: 53

Leu Gln Tyr Asp Asn Leu Pro Arg Thr
1               5

<210> SEQ ID NO 54
<211> LENGTH: 11
<212> TYPE: PRT
<213> ORGANISM: Mus musculus

<400> SEQUENCE: 54

Arg Ala Ser His Ser Ile Ser Asn Phe Leu His
1               5                   10

<210> SEQ ID NO 55
<211> LENGTH: 7
<212> TYPE: PRT
<213> ORGANISM: Mus musculus

<400> SEQUENCE: 55

Tyr Ala Ser Gln Ser Ile Ser
1               5

<210> SEQ ID NO 56
<211> LENGTH: 9
<212> TYPE: PRT
<213> ORGANISM: Mus musculus

<400> SEQUENCE: 56

Gln Gln Ser Asn Ile Trp Ser Leu Thr
1               5

<210> SEQ ID NO 57
<211> LENGTH: 15
<212> TYPE: PRT
<213> ORGANISM: Mus musculus

<400> SEQUENCE: 57

Arg Ala Ser Glu Ser Val Glu Tyr Tyr Gly Thr Ser Leu Met Gln
1               5                   10                  15

<210> SEQ ID NO 58
<211> LENGTH: 7
<212> TYPE: PRT
<213> ORGANISM: Mus musculus

<400> SEQUENCE: 58

Gly Ala Ser Asn Val Glu Ser
1               5

<210> SEQ ID NO 59
<211> LENGTH: 9
<212> TYPE: PRT
<213> ORGANISM: Mus musculus

```
<400> SEQUENCE: 59

Gln Gln Ser Arg Lys Val Pro Tyr Thr
1               5


<210> SEQ ID NO 60
<211> LENGTH: 9
<212> TYPE: PRT
<213> ORGANISM: Mus musculus

<400> SEQUENCE: 60

Ser Gln Asn Thr His Val Pro Pro Thr
1               5


<210> SEQ ID NO 61
<211> LENGTH: 16
<212> TYPE: PRT
<213> ORGANISM: Mus musculus

<400> SEQUENCE: 61

Lys Ser Ser Lys Ser Leu Leu His Ser Asn Gly Asn Thr Tyr Leu Asn
1               5                   10                  15


<210> SEQ ID NO 62
<211> LENGTH: 7
<212> TYPE: PRT
<213> ORGANISM: Mus musculus

<400> SEQUENCE: 62

Trp Met Ser Asn Leu Ala Ser
1               5


<210> SEQ ID NO 63
<211> LENGTH: 9
<212> TYPE: PRT
<213> ORGANISM: Mus musculus

<400> SEQUENCE: 63

Met Gln His Ile Glu Tyr Pro Phe Thr
1               5


<210> SEQ ID NO 64
<211> LENGTH: 16
<212> TYPE: PRT
<213> ORGANISM: Mus musculus

<400> SEQUENCE: 64

Arg Ser Ser Lys Ser Leu Leu His Ser Tyr Asp Ile Thr Tyr Leu Tyr
1               5                   10                  15


<210> SEQ ID NO 65
<211> LENGTH: 9
<212> TYPE: PRT
<213> ORGANISM: Mus musculus

<400> SEQUENCE: 65

Ala Gln Asn Leu Glu Leu Pro Pro Thr
1               5


<210> SEQ ID NO 66
<211> LENGTH: 10
<212> TYPE: PRT
<213> ORGANISM: Mus musculus

<400> SEQUENCE: 66
```

```
Ser Ala Ser Ser Ser Val Ser Tyr Met Tyr
1               5                   10


<210> SEQ ID NO 67
<211> LENGTH: 7
<212> TYPE: PRT
<213> ORGANISM: Mus musculus

<400> SEQUENCE: 67

Asp Thr Ser Asn Leu Ala Ser
1               5


<210> SEQ ID NO 68
<211> LENGTH: 9
<212> TYPE: PRT
<213> ORGANISM: Mus musculus

<400> SEQUENCE: 68

Gln Gln Trp Ser Ser Tyr Pro Leu Thr
1               5


<210> SEQ ID NO 69
<211> LENGTH: 16
<212> TYPE: PRT
<213> ORGANISM: Mus musculus

<400> SEQUENCE: 69

Lys Ser Ser Gln Ser Leu Leu His Ser Asp Gly Lys Thr Phe Leu Asn
1               5                   10                  15


<210> SEQ ID NO 70
<211> LENGTH: 7
<212> TYPE: PRT
<213> ORGANISM: Mus musculus

<400> SEQUENCE: 70

Leu Val Ser Arg Leu Asp Ser
1               5


<210> SEQ ID NO 71
<211> LENGTH: 9
<212> TYPE: PRT
<213> ORGANISM: Mus musculus

<400> SEQUENCE: 71

Cys Gln Gly Thr His Phe Pro Arg Thr
1               5


<210> SEQ ID NO 72
<211> LENGTH: 16
<212> TYPE: PRT
<213> ORGANISM: Mus musculus

<400> SEQUENCE: 72

Arg Ser Ser Gln Ser Ile Val His Ser Asn Gly Asn Thr Tyr Leu Glu
1               5                   10                  15


<210> SEQ ID NO 73
<211> LENGTH: 9
<212> TYPE: PRT
<213> ORGANISM: Mus musculus

<400> SEQUENCE: 73

Phe Gln Gly Ser His Val Pro Trp Thr
```

-continued 1 5

<210> SEQ ID NO 74
<211> LENGTH: 345
<212> TYPE: DNA
<213> ORGANISM: Artificial Sequence
<220> FEATURE:
<223> OTHER INFORMATION: Mouse-human chimeric antibody H chain

<400> SEQUENCE: 74
caggtgcagc tggtggagtc tggagctgag gtgaagaagc ctggggcctc agtgaaggtc 60
tcctgcaagg cttctggata caccttcacc gactatgaaa tgcactgggt gcgacaggcc 120
cctggacaag ggcttgagtg gatgggagct cttgatccta aaactggtga tactgcctac 180
agtcagaagt tcaagggcag agtcacgatt accgcggacg aatccacgag cacagcctac 240
atggagctga gcagcctgag atctgaggac acggccgtgt attactgtgc gagattctac 300
tcctatactt actggggcca gggaaccctg gtcaccgtct cctca 345

<210> SEQ ID NO 75
<211> LENGTH: 345
<212> TYPE: DNA
<213> ORGANISM: Artificial Sequence
<220> FEATURE:
<223> OTHER INFORMATION: Mouse-human chimeric antibody H chain

<400> SEQUENCE: 75
caggtgcagc tggtggagtc tggagctgag gtgaagaagc ctggggcctc agtgaaggtc 60
tcctgcaagg cttctggata caccttcacc gactatgaaa tgcactgggt gcgacaggcc 120
cctggacaag ggcttgagtg gatgggagct cttgatccta aaactggtga tactgcctac 180
agtcagaagt tcaagggcag agtcacgctg accgcggacg aatccacgag cacagcctac 240
atggagctga gcagcctgag atctgaggac acggccgtgt attactgtac aagattctac 300
tcctatactt actggggcca gggaaccctg gtcaccgtct cctca 345

<210> SEQ ID NO 76
<211> LENGTH: 345
<212> TYPE: DNA
<213> ORGANISM: Artificial Sequence
<220> FEATURE:
<223> OTHER INFORMATION: Mouse-human chimeric antibody H chain

<400> SEQUENCE: 76
caggtgcagc tggtggagtc tggagctgag gtgaagaagc ctggggcctc agtgaaggtc 60
tcctgcaagg cttctggata caccttcacc gactatgaaa tgcactgggt gcgacaggcc 120
cctggacaag ggcttgagtg gatgggagct cttgatccta aaactggtga tactgcctac 180
agtcagaagt tcaagggcag agtcacgctg accgcggaca aatccacgag cacagcctac 240
atggagctga gcagcctgag atctgaggac acggccgtgt attactgtac aagattctac 300
tcctatactt actggggcca gggaaccctg gtcaccgtct cctca 345

<210> SEQ ID NO 77
<211> LENGTH: 345
<212> TYPE: DNA
<213> ORGANISM: Artificial Sequence
<220> FEATURE:
<223> OTHER INFORMATION: Mouse-human chimeric antibody H chain

<400> SEQUENCE: 77
caggtgcagc tggtggagtc tggagctgag gtgaagaagc ctggggcctc agtgaaggtc 60

-continued

```
tcctgcaagg cttctggata caccttcacc gactatgaaa tgcactgggt gcgacaggcc    120

cctggacaag ggcttgagtg gatgggagct cttgatccta aaactggtga tactgcctac    180

agtcagaagt tcaagggcag agtcacgctg accgcggaca aatccacgag cacagcctac    240

atggagctga gcagcctgac atctgaggac acggccgtgt attactgtac aagattctac    300

tcctatactt actggggcca gggaaccctg gtcaccgtct cctca                    345
```

```
<210> SEQ ID NO 78
<211> LENGTH: 345
<212> TYPE: DNA
<213> ORGANISM: Artificial Sequence
<220> FEATURE:
<223> OTHER INFORMATION: Mouse-human chimeric antibody H chain

<400> SEQUENCE: 78

caggtgcagc tggtgcagtc tggagctgag gtgaagaagc ctggggcctc agtgaaggtc     60

tcctgcaagg cttctggata caccttcacc gactatgaaa tgcactgggt gcgacaggcc    120

cctggacaag ggcttgagtg gatgggagct cttgatccta aaactggtga tactgcctac    180

agtcagaagt tcaagggcag agtcacgctg accgcggacg aatccacgag cacagcctac    240

atggagctga gcagcctgag atctgaggac acggccgtgt attactgtac aagattctac    300

tcctatactt actggggcca gggaaccctg gtcaccgtct cctca                    345
```

```
<210> SEQ ID NO 79
<211> LENGTH: 345
<212> TYPE: DNA
<213> ORGANISM: Artificial Sequence
<220> FEATURE:
<223> OTHER INFORMATION: Mouse-human chimeric antibody H chain

<400> SEQUENCE: 79

caggtgcagc tggtgcagtc tggagctgag gtgaagaagc ctggggcctc agtgaaggtc     60

tcctgcaagg cttctggata caccttcacc gactatgaaa tgcactgggt gcgacaggcc    120

cctggacaag ggcttgagtg gatgggagct cttgatccta aaactggtga tactgcctac    180

agtcagaagt tcaagggcag agtcacgctg accgcggaca aatccacgag cacagcctac    240

atggagctga gcagcctgag atctgaggac acggccgtgt attactgtac aagattctac    300

tcctatactt actggggcca gggaaccctg gtcaccgtct cctca                    345
```

```
<210> SEQ ID NO 80
<211> LENGTH: 345
<212> TYPE: DNA
<213> ORGANISM: Artificial Sequence
<220> FEATURE:
<223> OTHER INFORMATION: Mouse-human chimeric antibody H chain

<400> SEQUENCE: 80

caggtgcagc tggtgcagtc tggagctgag gtgaagaagc ctggggcctc agtgaaggtc     60

tcctgcaagg cttctggata caccttcacc gactatgaaa tgcactgggt gcgacaggcc    120

cctggacaag ggcttgagtg gatgggagct cttgatccta aaactggtga tactgcctac    180

agtcagaagt tcaagggcag agtcacgctg accgcggaca aatccacgag cacagcctac    240

atggagctga gcagcctgac atctgaggac acggccgtgt attactgtac aagattctac    300

tcctatactt actggggcca gggaaccctg gtcaccgtct cctca                    345
```

```
<210> SEQ ID NO 81
```

<211> LENGTH: 115
<212> TYPE: PRT
<213> ORGANISM: Artificial Sequence
<220> FEATURE:
<223> OTHER INFORMATION: Mouse-human chimeric antibody H chain

<400> SEQUENCE: 81

```
Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Tyr Ser Tyr Thr Tyr Trp Gly Gln Gly Thr Leu Val Thr
            100                 105                 110

Val Ser Ser
        115
```

<210> SEQ ID NO 82
<211> LENGTH: 115
<212> TYPE: PRT
<213> ORGANISM: Artificial Sequence
<220> FEATURE:
<223> OTHER INFORMATION: Mouse-human chimeric antibody H chain

<400> SEQUENCE: 82

```
Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115
```

<210> SEQ ID NO 83
<211> LENGTH: 115
<212> TYPE: PRT
<213> ORGANISM: Artificial Sequence
<220> FEATURE:
<223> OTHER INFORMATION: Mouse-human chimeric antibody H chain

<400> SEQUENCE: 83

```
Gln Val Gln Leu Val Glu Ser Gly Ala Glu Val Lys Lys Pro Gly Ala
1               5                   10                  15
```

-continued

```
Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115


<210> SEQ ID NO 84
<211> LENGTH: 115
<212> TYPE: PRT
<213> ORGANISM: Artificial Sequence
<220> FEATURE:
<223> OTHER INFORMATION: Mouse-human chimeric antibody H chain

<400> SEQUENCE: 84

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115


<210> SEQ ID NO 85
<211> LENGTH: 115
<212> TYPE: PRT
<213> ORGANISM: Artificial Sequence
<220> FEATURE:
<223> OTHER INFORMATION: Mouse-human chimeric antibody H chain

<400> SEQUENCE: 85

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115


<210> SEQ ID NO 86
<211> LENGTH: 115
<212> TYPE: PRT
<213> ORGANISM: Artificial Sequence
<220> FEATURE:
<223> OTHER INFORMATION: Mouse-human chimeric antibody H chain

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115


<210> SEQ ID NO 87
<211> LENGTH: 115
<212> TYPE: PRT
<213> ORGANISM: Artificial Sequence
<220> FEATURE:
<223> OTHER INFORMATION: Mouse-human chimeric antibody H chain

<400> SEQUENCE: 87

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115
```

-continued

<210> SEQ ID NO 88
<211> LENGTH: 336
<212> TYPE: DNA
<213> ORGANISM: Artificial Sequence
<220> FEATURE:
<223> OTHER INFORMATION: Mouse-human chimeric antibody L chain

<400> SEQUENCE: 88

```
gatgttgtga tgactcagtc tccactctcc ctgcccgtca cccctggaga gccggcctcc     60

atctcctgca gatctagtca gagccttgta cacagtaatg gaaacaccta tttacattgg    120

tacctgcaga agccagggca gtctccacag ctcctgatct ataaagtttc caaccgattt    180

tctggggtcc ctgacaggtt cagtggcagt ggatcaggca cagattttac actgaaaatc    240

agcagagtgg aggctgagga tgttggggtt tattactgct ctcaaaatac acatgttcct    300

cctacgtttg gccaggggac caagctggag atcaaa                              336
```

<210> SEQ ID NO 89
<211> LENGTH: 112
<212> TYPE: PRT
<213> ORGANISM: Artificial Sequence
<220> FEATURE:
<223> OTHER INFORMATION: Mouse-human chimeric antibody L chain

<400> SEQUENCE: 89

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110
```

<210> SEQ ID NO 90
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 90

```
Arg Ser Ser Gln Ser Leu Val His Ser Asn Ala Asn Thr Tyr Leu His
1               5                   10                  15
```

<210> SEQ ID NO 91
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 91

```
Arg Ser Ser Gln Ser Leu Val His Ser Asn Asp Asn Thr Tyr Leu His
1               5                   10                  15
```

-continued

<210> SEQ ID NO 92
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 92

Arg Ser Ser Gln Ser Leu Val His Ser Asn Glu Asn Thr Tyr Leu His
1 5 10 15

<210> SEQ ID NO 93
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 93

Arg Ser Ser Gln Ser Leu Val His Ser Asn Phe Asn Thr Tyr Leu His
1 5 10 15

<210> SEQ ID NO 94
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 94

Arg Ser Ser Gln Ser Leu Val His Ser Asn His Asn Thr Tyr Leu His
1 5 10 15

<210> SEQ ID NO 95
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 95

Arg Ser Ser Gln Ser Leu Val His Ser Asn Asn Asn Thr Tyr Leu His
1 5 10 15

<210> SEQ ID NO 96
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 96

Arg Ser Ser Gln Ser Leu Val His Ser Asn Thr Asn Thr Tyr Leu His
1 5 10 15

<210> SEQ ID NO 97
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 97

Arg Ser Ser Gln Ser Leu Val His Ser Asn Gln Asn Thr Tyr Leu His
1 5 10 15

<210> SEQ ID NO 98

<211> LENGTH: 16
<212> TYPE: PRT
<213> ORGANISM: Artificial Sequence
<220> FEATURE:
<223> OTHER INFORMATION: mutant antibody L chain

<400> SEQUENCE: 98

```
Arg Ser Ser Gln Ser Leu Val His Ser Asn Ile Asn Thr Tyr Leu His
1               5                   10                  15
```

<210> SEQ ID NO 99
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 99

```
Arg Ser Ser Gln Ser Leu Val His Ser Asn Lys Asn Thr Tyr Leu His
1               5                   10                  15
```

<210> SEQ ID NO 100
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 100

```
Arg Ser Ser Gln Ser Leu Val His Ser Asn Leu Asn Thr Tyr Leu His
1               5                   10                  15
```

<210> SEQ ID NO 101
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 101

```
Arg Ser Ser Gln Ser Leu Val His Ser Asn Ser Asn Thr Tyr Leu His
1               5                   10                  15
```

<210> SEQ ID NO 102
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 102

```
Arg Ser Ser Gln Ser Leu Val His Ser Asn Trp Asn Thr Tyr Leu His
1               5                   10                  15
```

<210> SEQ ID NO 103
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 103

```
Arg Ser Ser Gln Ser Leu Val His Ser Asn Tyr Asn Thr Tyr Leu His
1               5                   10                  15
```

<210> SEQ ID NO 104
<211> LENGTH: 16

-continued

<212> TYPE: PRT
<213> ORGANISM: Artificial Sequence
<220> FEATURE:
<223> OTHER INFORMATION: mutant antibody L chain

<400> SEQUENCE: 104

```
Arg Ser Ser Gln Ser Leu Val His Ser Asn Arg Asn Thr Tyr Leu His
1               5                   10                  15
```

<210> SEQ ID NO 105
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 105

```
Arg Ser Ser Gln Ser Leu Val His Ser Asn Val Asn Thr Tyr Leu His
1               5                   10                  15
```

<210> SEQ ID NO 106
<211> LENGTH: 16
<212> TYPE: PRT
<213> ORGANISM: Artificial Sequence
<220> FEATURE:
<223> OTHER INFORMATION: mutant antibody L chain

<400> SEQUENCE: 106

```
Arg Ser Ser Gln Ser Leu Val His Ser Asn Pro Asn Thr Tyr Leu His
1               5                   10                  15
```

<210> SEQ ID NO 107
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 107

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Ala Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110
```

<210> SEQ ID NO 108
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 108

```
Asp Val Val Met Thr Gln Ser Pro Leu Ser Leu Pro Val Thr Pro Gly
1               5                   10                  15
```

```
Glu Pro Ala Ser Ile Ser Cys Arg Ser Ser Gln Ser Leu Val His Ser
            20                  25                  30

Asn Asp Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110


<210> SEQ ID NO 109
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 109

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Glu Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110


<210> SEQ ID NO 110
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 110

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Phe Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
```

```
            100                 105                 110


<210> SEQ ID NO 111
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 111

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn His Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110


<210> SEQ ID NO 112
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 112

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Asn Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110


<210> SEQ ID NO 113
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 113

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30
```

```
Asn Thr Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110


<210> SEQ ID NO 114
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 114

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gln Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110


<210> SEQ ID NO 115
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 115

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Ile Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110
```

<210> SEQ ID NO 116
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 116

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Lys Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110
```

<210> SEQ ID NO 117
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 117

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Leu Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110
```

<210> SEQ ID NO 118
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 118

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Ser Asn Thr Tyr Leu His Trp Tyr Leu Gln Lys Pro Gly Gln Ser
        35                  40                  45
```

```
Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110


<210> SEQ ID NO 119
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 119

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Trp Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110


<210> SEQ ID NO 120
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 120

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Tyr Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110


<210> SEQ ID NO 121
<211> LENGTH: 112
<212> TYPE: PRT
```

<213> ORGANISM: Artificial Sequence
<220> FEATURE:
<223> OTHER INFORMATION: mutant antibody L chain

<400> SEQUENCE: 121

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110
```

<210> SEQ ID NO 122
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 122

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Val Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110
```

<210> SEQ ID NO 123
<211> LENGTH: 112
<212> TYPE: PRT
<213> ORGANISM: Artificial Sequence
<220> FEATURE:
<223> OTHER INFORMATION: mutant antibody L chain

<400> SEQUENCE: 123

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Pro Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60
```

```
Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110


<210> SEQ ID NO 124
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 124

cttgtacaca gtgacggaaa cacctat                                          27


<210> SEQ ID NO 125
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 125

ataggtgttt ccgtcactgt gtacaag                                          27


<210> SEQ ID NO 126
<211> LENGTH: 10939
<212> TYPE: DNA
<213> ORGANISM: Cricetulus griseus

<400> SEQUENCE: 126

gagctcaatt aaccctcact aaagggagtc gactcgatcc tttacagaaa acttgcaaac     60

cctcttggag tagaaaagta gtagtatctg acacaagtat cagcaaaatg caaacttctc    120

cccatcccca gaaaaccatt ataaaaaccc ccatatctta tgcccaactg tagtgatata    180

ttatttatga tttattaaaa cttgcttaag gattcagaaa gcaaagtcag ccttaagcta    240

tagagaccag gcagtcagtg gtggtacaca cctttaatcc caggactcag gattaagaag    300

tagacggacc tctgttagtt caagtctacc attacctaca caagagtgaa gagtaaccga    360

tctcatgcct ttgatcccag cagctgggat catgtgcatt caatcccagc attcgggagt    420

tatataagac aggagcaagg tctcagagct ggcattcatt ctccagccac attgaggata    480

ggaaaacatt gaagtgtcag gatgctgagg agaggcagca gtttgaggtt tggtagaacc    540

aggatcacct tttggtctga ggtagagtaa gaactgtggc tggctgcttt gcttttctga    600

tcttcagctt gaagcttgaa ctccaatatt tgtctctggg tctattatta tcatgttaca    660

cctaacttta aagctgattt acgcaagaca gttgtaggtg gacctttctt tcctgcccac    720

cagttcccaa ataactgaca cggagactca atattaatta taaatgattg gttaatagct    780

cagtcttgtt actggctaac tcttacattt taaattaact catttccatc cctttacttg    840

ctgccatgtg gttcatggct tgttcaagtc ctgcttcttc tgtctctggc tggtgatgcc    900

tctggttctg ccctttatcc cagaattctc ctagtctggc tctcctgccc agctataggc    960

cagtcagctg tttattaacc aatgagaata atacatattt atagtgtaca aagattgctc   1020

ctcaacaccc aatttttttat gtgcaacctg agaatctgga ctcattgccc tcatgcttgc  1080

agaggcggca cccttaccca ctaagccacc tttctagccc tgttgctttt gttttttgag   1140
```

-continued

```
acaggttcca ctatgtagcc caggctggcc tcaaactgac cattctcctg cctaaacctc   1200
ccgaacactg gaattatagt caaggcctac ctgccctggc attttcacac ttttatttcc   1260
tggctgagtc cattgacttt acactcatca aggttgaacc agttggagtt taattacagt   1320
gccaatcgca ctgaatccca cataatcaaa caacttcaag gaagcaaaaa accagttttt   1380
cctgaagatc aatgtcagct tgcctgattc agaatagacc cccgaaaaaa ggcaaatgct   1440
tgataaccaa tttcttctta ttgttcaatc ccctgctgct gtgtgtaagc tcctgagaaa   1500
ggacagtaag gggacattca tgatcagaga aagagcccca actccccccc cagccccacc   1560
cccaccctgt ccacagtctg ttggtttggt ttcccccctgg ctgacaccca gaaatcacaa   1620
cataatcacc taggtcactg taacaagttc ctttctggaa aatgctacaa atgatattgg   1680
taacatgagt aatgaataat gcctggagtc caactccctt gtgacccagc aatgttttcc   1740
gtgggtgctc ccttccccag ctgcaggcct gacatgtacc ttaaaaagcc tcccctggag   1800
gacagaattt tgtgggtact atagtgttct cacaaatact tcccctaata cccttactta   1860
gttaccataa ataacatgca gcccctggtg aggcacacag ggctccaatg tacagcttct   1920
cagacactgc aggaaccttc ctctcctaat gcagcactgg tctcttcagg ctggacagca   1980
ggaacccata ccactccaat cctagtgtgg agtagagctg tctacgaaaa ccagcagatc   2040
tatagctaaa tgtgtttcaa ttttatgctt tgacaaattg tactgacccc acccccaccc   2100
cttccccctt gctgtgctgg gaattgaacc caggaccttg tgcatgccag gcaagtactc   2160
taacactgag ctatagcccc aatctttcat ccaagtctct atgtgtgccc acactcgctt   2220
tttattttga gacaaaaggt tcttattttg agataaggtc tcactatgtt gccttgactt   2280
ttttttttt tttttttga acttttgacc ttcctacctc agctgagact acaagtcttt   2340
taccatcagg cccggctgat ggtaaaataa cagtatttga aatagtttaa acacatcatc   2400
ttaatggtca accacacaat ttccgaaatg ttgctggctc agtctggggc aaacctgtcc   2460
gccccaacat tggtgctagg aagaaagcac agacaagtag ccctcccagc tcaggagtaa   2520
aagacctgga gggggtggcc cacttcggtc aagttcacgg gatggggagg ggtaccctcc   2580
tccagtagtg gtggtatttg gcagttcctc caccgacgcc ctctggaagc acctgcttgg   2640
acccgcaaag ccaggaatgc agcttcctca agggactcgc cagcgagggt aacaggacag   2700
aggcgtccca agagggctgg ggcggaaggg ggaagacagg gtcggcctta gatagggcaa   2760
agggccttct ggctgtgttc ccggggtaac cgccccacca cgcctggagc ccgacgtggc   2820
gagcgatggg gacagcgagc aggaagtcgt actggggagg gccgcgtagc agatgcagcc   2880
gagggcggcg ctgccaggta cacccgaggg caccgcgggg gtgagcgcca ggtccctgaa   2940
ccagccaggc ctccagagcc gagtccggcg gaccgacggt acgttctgga atgggaaggg   3000
atccgggaca ccgaattgct gcattgaggg gctcagaggt tctgatgtgg gagtccagaa   3060
agggttttat ctaccggagg tgatgtgact tccggcctct ggaagtgctg ttggagtctc   3120
tgggaccttg ggtcctctcg actaggtttg gaaggggtga aataggggta gggagaaagg   3180
agaggactgc agcaatgtct tcccgaacga cctgggttcg ggaggggtcg aaggacaagg   3240
ggctgttgtg gggggtcttc agacgcggag gggtggtatt ctattttctg ggaagatggt   3300
gtcgatgcac ttgaccaagt ctagtcgatc tgaagaggct aggggaacag acagtgagag   3360
aggatggtgg agggagtggc agaacccttc cagaaactgg gagaggctct agcacctgca   3420
accccttccc tggcctccgg ggagtcccag aagagggcag gaccatggac acaggtgcat   3480
```

-continued

```
tcgtgccggc gcgctccggc ctggcgaagg tgcgcgctct tggaggccgc gggagggcca   3540
gacgcgcgcc cggagagctg gccctttaag gctacccgga ggcgtgtcag gaaatgcgcc   3600
ctgagcccgc ccctcccgga acgcggcccg agacctggca agctgagacg gaactcggaa   3660
ctagcactcg gctcgcggcc tcggtgaggc cttgcgcccg ccatgcctct gtcattgccc   3720
ctcgggccgc ctccctgaac ctccgtgacc gccctgcagt cctccctccc ccccttcgac   3780
tcggcgggcg cttccgggcg ctcccgcagc ccgccctcca cgtagcccac acctccctct   3840
cggcgctccg cttcccacgc ggtccccgac ctgttctttc ctcctccacc ctgcccttct   3900
gtccctctcc cttcctttct cccctcgact cgtccctatt aggcaacagc ccctgtggtc   3960
cagccggcca tggctgtcaa ggctcacacc cttagctagg ccccttctcc cttccctggg   4020
tcttgtctca tgacccctg ccccgcccgg gagcgagcgc gatgtggagc agtgcctctg   4080
gcaagcagaa cttcacccaa gccatgtgac aattgaaggc tgtacccca gaccctaaca   4140
tcttggagcc ctgtagacca gggagtgctt ctggccgtgg ggtgacctag ctcttctacc   4200
accatgaaca gggcccctct gaagcggtcc aggatcctgc gcatggcgct gactggaggc   4260
tccactgcct ctgaggaggc agatgaagac agcaggaaca agccgtttct gctgcgggcg   4320
ctgcagatcg cgctggtcgt ctctctctac tgggtcacct ccatctccat ggtattcctc   4380
aacaagtacc tgctggacag cccctccctg cagctggata cccctatctt cgtcactttc   4440
taccaatgcc tggtgacctc tctgctgtgc aagggcctca gcactctggc cacctgctgc   4500
cctggcaccg ttgacttccc caccctgaac ctggacctta aggtggcccg cagcgtgctg   4560
ccactgtcgg tagtcttcat tggcatgata agtttcaata acctctgcct caagtacgta   4620
ggggtggcct tctacaacgt ggggcgctcg ctcaccaccg tgttcaatgt gcttctgtcc   4680
tacctgctgc tcaaacagac cacttccttc tatgccctgc tcacatgtgg catcatcatt   4740
ggtgagtggg gcccgggggc tgtgggagca ggatgggcat cgaactgaag ccctaaaggt   4800
caacactgta ggtaccttta cttactgtcc caggtccctt gcatcagcag ttacaggaag   4860
agccctgtag aaaacaaata acttccttat ggtcattcaa caagttaggg acccagccag   4920
ggtgaaaata atgttagcag caactacagc aaagatggct ctcgccactt gcatgattaa   4980
aatgtgccag gtactcagat ctaagcattg gatccacatt aactcaacta atccctatta   5040
caaggtaaaa tatatccgaa ttttacagag ggaaaaccaa ggcacagaga ggctaagtag   5100
cttgaccagg atcacacagc taataatcac tgacatagct gggatttaaa cataagcagt   5160
tacctccata gatcacacta tgaccaccat gccactgttc cttctcaaga gttccaggat   5220
cctgtctgtc cagttctctt taaagaggac aacacatctg acattgctac cttgaggtaa   5280
catttgaaat agtgggtaga catatgtttt aagttttatt cttacttttt atgtgtgtgt   5340
gtttgggggg ccaccacagt gtatgggtgg agataagggg acaacttaag aattggtcct   5400
ttctcccacc acatgggtgc tgaggtctga actcaggtca tcaggattgg cacaaatccc   5460
tttacccact gagccatttc actggtccaa tatatgtgtg cttttaagag gctttaacta   5520
ttttcccaga tgtgaatgtc ctgctgatca ttatcccctt ttacccggaa gccctctggg   5580
aggtgccatc cctgtggtcg tctgcataca aatggggaaa ctgcaactca gagaaacaag   5640
gctacttgcc agggccccac aagtaagata ggctgggatg ccatcccaga ctggccacac   5700
tccctggcct gtgcttcaag ccagtttact ttgttcctgc ccattggaag ttagcatgtt   5760
gcagtcaaac acaataacta caggccaaaa gtgcttttaa attaaagtca gatgaacttt   5820
taaacatcca gagctcctca actgcaggag ttacaacctg attctgcaac catctttgca   5880
```

-continued

```
gtgcccggta gtcatatgta gctagaggct cttggctagg acagcatgtg ttaggaaaca   5940
tctggccctg agatcattga attgagtgac tgctgggtga caaagaccaa ggcatccgtt   6000
ccctgagagt cctgggcaag cagcaatgtg accttcattt gtacctactc aggttcttta   6060
tctgtcctgt ttgacctact tagtctcctc tggtgtctca gaggcccagg ctgggtactc   6120
tggatgtcag gatcaggcca atgcgcacat ctgccctaga aatgtccccc tggttgagca   6180
gctcctgaat ccatcggtaa agggtctgga ccagggagga gtcagataaa aagctgacag   6240
cactggggga ctccatgggg aactcccacc tgcccccaca catccatcct aagagaactg   6300
gtattccttg tttcctcttt gtcctacaag gcaccctggg atcccacttc agtctcccag   6360
ccttgccagg gttagagggc atgagcctcc ttgtggggaa tttagatgca agaaggtaca   6420
gtcactagag aacctgagct cagatcccca aagtaaccag tacctgatag tgaggcagct   6480
gagaaccgca gcagcctgcc tgagtggctg aactctgcgg cctccggaac tggccccaac   6540
tgttgggtct cctcttcctt cctcctgtga gggagggccc atctctgata agtgctgtgg   6600
ggactctaga gtagggagga ggaggagcaa tctaagcagg ccttactgag aagtccttgc   6660
tggcatgtgg ctgcctgagg agtacagact gggaacaccc atttgaatga gtaaggtttt   6720
tcctgaaggc catggggagc cacggaggaa aatcatttta gttacaagac aaagagtaga   6780
ttggttaaca tgggagcaag gacatggccc caattttcat agatgaagga aattggaact   6840
cagagaggtt aagtaacttc tcccaaatag ctcagcttca aaatcacaga acagtcagag   6900
tctagatctc tctgatgcct gtgatggtcc tgccattcca tgttgctgat ccctgtggca   6960
tcagtaagcc tctaccttgt gggaatgcag gatctaaatg aagagaggaa gtgctggccc   7020
catgctgtgg tctggaaagc tatgcaggct ctttgagcag agagtgaccc acaagtgaat   7080
agagtcctat gagactcaaa gcaacatcca cccttaagca gctctaacca aatgctcaca   7140
ctgagggagc caaagccaag ttagagtcct gtgcttgccc aaggtcactt tgcctggccc   7200
tcctcctata gcacccgtgt tatcttatag ccctcattac agtgattaca attataatta   7260
gagaggtaac agggccacac tgtccttaca cattcccctg ctagattgta gctgggagag   7320
ggggagatgt aggtggctgg gggagtggga gggaagatgc agattttcat tctgggctct   7380
actccctcag ccatttttg gtgtgggagt tagactttgg atatgttgat gatgaggtaa    7440
gggccacaga acagtctgaa ctgtggtatc agaatcctgt ccctctccct ctctcctcat   7500
ccctcttcac cttgtcactc ctctgtctgc tacaggtggt ttctggctgg gtatagacca   7560
agagggagct gagggcaccc tgtccctcat aggcaccatc ttcggggtgc tggccagcct   7620
ctgcgtctcc ctcaatgcca tctataccaa gaaggtgctc ccagcagtgg acaacagcat   7680
ctggcgccta accttctata acaatgtcaa tgcctgtgtg ctcttcttgc ccctgatggt   7740
tctgctgggt gagctccgtg ccctccttga ctttgctcat ctgtacagtg cccacttctg   7800
gctcatgatg acgctgggtg gcctcttcgg ctttgccatt ggctatgtga caggactgca   7860
gatcaaattc accagtcccc tgacccacaa tgtatcaggc acagccaagg cctgtgcgca   7920
gacagtgctg gccgtgctct actatgaaga gactaagagc ttcctgtggt ggacaagcaa   7980
cctgatggtg ctgggtggct cctcagccta tacctgggtc aggggctggg agatgcagaa   8040
gacccaagag gaccccagct ccaaagaggg tgagaagagt gctattgggg tgtgagcttc   8100
ttcagggacc tgggactgaa cccaagtggg gcctacacag cactgaaggc ttcccatgga   8160
gctagccagt gtggccctga gcaatactgt ttacatcctc cttggaatat gatctaagag   8220
```

-continued

```
gagccagggt ctttcctggt aatgtcagaa agctgccaaa tctcctgtct gccccatctt   8280
gttttgggaa aaccctacca ggaatggcac ccctacctgc ctcctcctag agcctgtcta   8340
cctccatatc atctctgggg ttgggaccag ctgcagcctt aaggggctgg attgatgaag   8400
tgatgtcttc tacacaaggg agatgggttg tgatcccact aattgaaggg atttgggtga   8460
ccccacacct ctgggatcca gggcaggtag agtagtagct taggtgctat taacatcagg   8520
aacacctcag cctgcctttg aagggaagtg ggagcttggc caagggagga aatggccatt   8580
ctgccctctt cagtgtggat gagtatggca gacctgttca tggcagctgc accctggggt   8640
ggctgataag aaaacattca cctctgcatt tcatatttgc agctctagaa cgggggagag   8700
ccacacatct tttacgggtt aagtagggtg atgagctcct ccgcagtccc taaccccagc   8760
tttacctgcc tggcttccct tggcccagct acctagctgt actccctttc tgtactcttc   8820
tcttctccgt catggcctcc cccaacacct ccatctgcag gcaggaagtg gagtccactt   8880
gtaacctctg ttcccatgac agagcccttt gaatacctga acccctcatg acagtaagag   8940
acatttatgt tctctggggc tggggctgaa ggagcccact ggttctcact tagcctatct   9000
ggctcctgtc acaaaaaaaa aaaaagaaaa aaaaaaagca taaaccaagt tactaagaac   9060
agaagttggt ttataacgtt ctggggcagc aaagcccaga tgaagggacc catcgaccct   9120
ctctgtccat atcctcatgc tgcagaagta caggcaagct cctttaagcc tcatatagga   9180
acactagcct cactcatgag ggttttactc catgacctgt caacctcaaa gccttcaaca   9240
tgaggactcc aacgtaaatt tggggacaga agcactcaga ccatacccca gcaccacacc   9300
ctcctaacct cagggtagct gtcattctcc tagtctcctc tcttgggcct ttagaacccc   9360
catttccttg ggtaatgtc tgatgttttt gtccctgtca taaaaagatg gagagactgt   9420
gtccagcctt tgattcctac ttcctacaat cccaggttct aatgaagttt gtggggcctg   9480
atgccctgag ttgtatgtga tttaataata aaaaagcaag atacagcatg tgtgtggact   9540
gagtgagggc cacagggatc taaaagccaa gtgtgagggg acccagctac agcaggcagc   9600
atcctgagcc tggaatctct tcaggacaag aattctccat atacctacct actctgggga   9660
gtaggtggcc agagttcaag cttcccttag taccaactac cactggctgt gctcttactg   9720
aaggcagaca tggcactgag tgctgtccat ctgtcactca tctccacagc cattcctaat   9780
gtgtggggtg ggagccatca ccaaacccca ttttcagata aggacacagg ctcagagagg   9840
cttgtgtgga gaaaagtagc agcagaattc agagagctgg gtctcctgca gcaccttgga   9900
ctgccagcag ccacagtgct tgtcacacag cacatactca aaagaatgcc agccccctca   9960
gcctagagtg cctggccttt ctttcagatg aggaagaggg tcaaagctgt tagcttgccc  10020
accatatgac cacatacatg accaacagct tgagggaggg aggattactg tggctcccag  10080
cctgagaggt gggacaccca aatgtattag gtccttgaat cagggctgac cttgtgattc  10140
agtcactcct accagaatgc tggggaatgg ggatgccaaa ggcaaaggag gctttctaag  10200
gtgtggtgta agataggcat ttctgcttcc atgtacacct gtgagcagag taggaaggcc  10260
ctgtggagaa tatatcccac aaaccagtag cccttcctgg cagtgggtga atactgccac  10320
cctatacccc tatgcaaggc cagtagaacc acccaaccca caacatctag agaaattaca  10380
ggtcatctta agcctctaaa ttgtggagaa actcgacatg cgcacgattc ctaacctgct  10440
agcctagggt gcggggtgga taatttaagg aaactggggt ttcttataga atcggaggct  10500
ccatgaagtc accctgacaa gaggtcagca atagccagca gcagtggcta ctcctaagcc  10560
tccagacaga gcaccctgtg aatgtacctt attctcacat ctgggtgtct ataggtgtga  10620
```

```
ctgggtcaga tgtcacccag gccattgcaa tgggccctta gccccatggg gtgttgggat  10680

agcagccaag cagctcccat gctgagatac tgcctgcagt agactgatgg ataagaaaac  10740

aaggcccaaa atgttttctt tccagacttg atctttcttt gttcaaaaat gctgttttcc  10800

cttaaacttg cccaaaccca ttgttttgca gttgaggaaa ataaggcata gaaagattaa  10860

aggaagtttc tgaggttaca gagcaaagta ctggcttcac ctgaaataga caggtgtgcc  10920

ctgatcctga tttgagctc                                               10939


<210> SEQ ID NO 127
<211> LENGTH: 352
<212> TYPE: PRT
<213> ORGANISM: Cricetulus griseus

<400> SEQUENCE: 127

Met Ala Leu Thr Gly Gly Ser Thr Ala Ser Glu Glu Ala Asp Glu Asp
1               5                   10                  15

Ser Arg Asn Lys Pro Phe Leu Leu Arg Ala Leu Gln Ile Ala Leu Val
            20                  25                  30

Val Ser Leu Tyr Trp Val Thr Ser Ile Ser Met Val Phe Leu Asn Lys
        35                  40                  45

Tyr Leu Leu Asp Ser Pro Ser Leu Gln Leu Asp Thr Pro Ile Phe Val
    50                  55                  60

Thr Phe Tyr Gln Cys Leu Val Thr Ser Leu Leu Cys Lys Gly Leu Ser
65                  70                  75                  80

Thr Leu Ala Thr Cys Cys Pro Gly Thr Val Asp Phe Pro Thr Leu Asn
                85                  90                  95

Leu Asp Leu Lys Val Ala Arg Ser Val Leu Pro Leu Ser Val Val Phe
            100                 105                 110

Ile Gly Met Ile Ser Phe Asn Asn Leu Cys Leu Lys Tyr Val Gly Val
        115                 120                 125

Ala Phe Tyr Asn Val Gly Arg Ser Leu Thr Thr Val Phe Asn Val Leu
    130                 135                 140

Leu Ser Tyr Leu Leu Leu Lys Gln Thr Thr Ser Phe Tyr Ala Leu Leu
145                 150                 155                 160

Thr Cys Gly Ile Ile Ile Gly Gly Phe Trp Leu Gly Ile Asp Gln Glu
                165                 170                 175

Gly Ala Glu Gly Thr Leu Ser Leu Ile Gly Thr Ile Phe Gly Val Leu
            180                 185                 190

Ala Ser Leu Cys Val Ser Leu Asn Ala Ile Tyr Thr Lys Lys Val Leu
        195                 200                 205

Pro Ala Val Asp Asn Ser Ile Trp Arg Leu Thr Phe Tyr Asn Asn Val
    210                 215                 220

Asn Ala Cys Val Leu Phe Leu Pro Leu Met Val Leu Leu Gly Glu Leu
225                 230                 235                 240

Arg Ala Leu Leu Asp Phe Ala His Leu Tyr Ser Ala His Phe Trp Leu
                245                 250                 255

Met Met Thr Leu Gly Gly Leu Phe Gly Phe Ala Ile Gly Tyr Val Thr
            260                 265                 270

Gly Leu Gln Ile Lys Phe Thr Ser Pro Leu Thr His Asn Val Ser Gly
        275                 280                 285

Thr Ala Lys Ala Cys Ala Gln Thr Val Leu Ala Val Leu Tyr Tyr Glu
    290                 295                 300

Glu Thr Lys Ser Phe Leu Trp Trp Thr Ser Asn Leu Met Val Leu Gly
```

-continued

```
305                 310                 315                 320

Gly Ser Ser Ala Tyr Thr Trp Val Arg Gly Trp Glu Met Gln Lys Thr
                325                 330                 335

Gln Glu Asp Pro Ser Ser Lys Glu Gly Glu Lys Ser Ala Ile Gly Val
            340                 345                 350
```

```
<210> SEQ ID NO 128
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 128

ggatcctgcg catgaaaaag cctgaactca cc                                   32


<210> SEQ ID NO 129
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 129

gcggccgcct attcctttgc cctcggacg                                       29


<210> SEQ ID NO 130
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 130

atgcatgcca ccatgaaaaa gcctgaactc acc                                  33


<210> SEQ ID NO 131
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 131

ggatcccagg ctttacactt tatgcttc                                        28


<210> SEQ ID NO 132
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 132

gctgtctgga gtactgtgca tctgc                                           25


<210> SEQ ID NO 133
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 133

ggaatgcagc ttcctcaagg gactcgc                                         27
```

<210> SEQ ID NO 134
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 134
tgcatcaggt cggagacgct gtcgaac 27

<210> SEQ ID NO 135
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 135
gcactcgtcc gagggcaaag gaatagc 27

<210> SEQ ID NO 136
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 136
tgtgctggga attgaaccca ggac 24

<210> SEQ ID NO 137
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 137
ctacttgtct gtgctttctt cc 22

<210> SEQ ID NO 138
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 138
ctcgactcgt ccctattagg caacagc 27

<210> SEQ ID NO 139
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 139
tcagaggcag tggagcctcc agtcagc 27